(12) United States Patent
Kobayashi et al.

(10) Patent No.: US 8,318,967 B2
(45) Date of Patent: Nov. 27, 2012

(54) POLYSILANE-SUPPORTED TRANSITION METAL CATALYST FOR LIQUID PHASE REACTION

(75) Inventors: Shu Kobayashi, Tokyo (JP); Hidekazu Oyamada, Saitama (JP); Ryo Akiyama, Tokyo (JP); Takeshi Naito, Tokyo (JP)

(73) Assignee: Japan Science and Technology Agency, Saitama (JP)

(*) Notice: Subject to any disclaimer, the term of this patent is extended or adjusted under 35 U.S.C. 154(b) by 998 days.

(21) Appl. No.: 12/224,636

(22) PCT Filed: Feb. 27, 2007

(86) PCT No.: PCT/JP2007/053582
§ 371 (c)(1),
(2), (4) Date: Sep. 2, 2008

(87) PCT Pub. No.: WO2007/102334
PCT Pub. Date: Sep. 13, 2007

(65) Prior Publication Data
US 2009/0143607 A1    Jun. 4, 2009

(30) Foreign Application Priority Data

Mar. 2, 2006  (JP) ................. 2006-056393
Sep. 1, 2006  (JP) ................. 2006-237266

(51) Int. Cl.
*C07F 7/08* (2006.01)
*C07F 7/02* (2006.01)
*C07F 7/00* (2006.01)

(52) U.S. Cl. ................ 556/430; 556/173; 556/51

(58) Field of Classification Search ............... None
See application file for complete search history.

(56) References Cited

U.S. PATENT DOCUMENTS

| | | | |
|---|---|---|---|
| 5,017,654 A * | 5/1991 | Togashi et al. ............. 525/100 |
| 5,135,960 A * | 8/1992 | Higuchi et al. ............. 521/76 |
| 5,750,588 A * | 5/1998 | Takeoka et al. ............. 522/66 |
| 6,365,698 B1 * | 4/2002 | Goldslager et al. .......... 528/31 |

FOREIGN PATENT DOCUMENTS

| | | |
|---|---|---|
| EP | 0 352 493 | 1/1990 |
| EP | 0349898 | 8/1992 |
| JP | 2-9448 | 1/1990 |
| JP | H6-49215 | 2/1994 |
| JP | 11-306855 | 11/1999 |
| JP | 2001-253721 | 9/2001 |
| JP | 2002-4057 | 1/2002 |
| JP | 2002-66330 | 3/2002 |
| JP | 2002-134123 | 5/2002 |
| JP | 2003-147418 | 5/2003 |
| WO | WO2007/102334 | 9/2007 |

OTHER PUBLICATIONS

Kobayashi, S. et al. "Catalytic Asymmetric Dihydroxylation Using Phenoxyethoxymethyl-polystyrene (PEM)-Based Novel Microencapsulated Osmium Tetroxide (PEM-MC OsO4)," Organic Letters, (2001) 3: 2649-2652.*

Gao et al., "Rhodium—phosphine complex catalysts tethered on silica-supported heterogeneous metal catalysts: arene hydrogenation under atmospheric pressure," Journal of Molecular Catalysis A: Chemical, vol. 149, pp. 63-74 (1999).

Hagio et al., "Immobilization of a Platinum Catalyst Using the Polymer Incarceration (PI) Method and Application to Catalytic Reactions," Synlett, pp. 813-816 (2005).

Kleij et al., "The 'Dendritic Effect' in Homogeneous Catalysis with Carbosilane-Supported Arylnickel (II) Catalysts: Observation of Active Site Proximity Effects in Atom-Transfer Radical Addition," Angewandte Chemie. International Edition, vol. 39, No. 1, pp. 176-178 (2000).

Lewis et al., "Preparation and structure of platinum group metal colloids: without solvent," Chem. Mater., vol. 1, No. 1, pp. 106-114 (1989).

Notification of Transmittal of Translation of the International Preliminary Report on Patentability corresponding to International Application No. PCT/JP2007/053582 dated Oct. 23,2008.

Okamoto et al., "Formation of Nanoarchitectures Including Subnanometer Palladium Clusters and Their Use as Highly Active Catalysts," J. Am. Chem. Soc., vol. 127, pp. 2125-2135 (2005).

Sanji et al., "Metal Nanoparticles Derived from Polysilane Shell Cross-linked Micelle Templates," Chemistry Letters, vol. 32, No. 10, pp. 980-981 (2003).

West, R., "The Polysilane High Polymers," J. Organomet. Chem., vol. 300, pp. 327-346 (1986). Supplementary European Search Report corresponding to European Application No. 07714975.5-2104 dated Feb. 11, 2009.

Hagio, H., et al., Practical Preparation Method of Polymer-Incarcerated (PI) Palladium Catalysts Using Pd(II) Salts. *Organic Letters*. vol. 8, No. 3 pp. 375-378 (2006).

Oyamada et al., Polysilane-Supported Pd and Pt nanoparticles as efficient catalysts for organic synthesis. *Chemical Communications*. vol. 41, No. 4 pp. 4297-4299 (2006).

International Search Report corresponding to International Patent Application No. PCT/JP2007/053582 dated May 15, 2007.

* cited by examiner

*Primary Examiner* — Johann Richter
*Assistant Examiner* — James Meadows
(74) *Attorney, Agent, or Firm* — Jenkins, Wilson, Taylor & Hunt, P.A.

(57) ABSTRACT

The present invention provides a polysilane-supported transition metal catalysts or a polysilane/inorganic compound-supported transition metal catalysts, wherein various types of transition metals are supported by polysilane compounds, or combination of polysilanes and inorganic compounds. The catalysts of the present invention are hardly soluble in hydrocarbons and alcohols and are useful as catalysts in heterogeneous system for various organic synthetic reactions using the above solvents. Polysilanes supporting transition metals are easily crosslinkable by thermal treatment, microwave irradiation, UV irradiation or chemical methods such as hydrosilylation reaction and are changed to be insoluble in various solvents keeping high catalytic activity. Moreover, the stability and operability of polysilane-supported transition metal catalysts will be improved by the support thereof on inorganic compounds. These polysilane-supported transition metal catalysts show a high catalytic activity in hydrogenation reaction, hydrosilylation reaction, Heck reaction, Suzuki-Miyaura coupling reactions and the like. The catalyst is easily recoverable and reusable and the leakage of metals is extremely few.

7 Claims, No Drawings

POLYSILANE-SUPPORTED TRANSITION METAL CATALYST FOR LIQUID PHASE REACTION

RELATED APPLICATIONS

The application is the U.S. National Stage of International Application No. PCT/JP2007/053582, filed on Feb. 27, 2007, which claims priority to Japanese Patent Application No. 2006-056393, filed on Mar. 2, 2006, and Japanese Patent Application No. 2006-237266, filed on Sep. 1, 2006.

FIELD OF THE INVENTION

The present invention relates to a polysilane-supported transition metal catalyst with a high catalytic activity, which is easily prepared on a massive scale and handled, and is recoverable, reusable or usable continuously for long time, and the use thereof.

PRIOR ART

Although transition metals play important roles in various chemical reactions as catalysts, the metals and ligands thereof are often expensive. Furthermore, transition metal nano-size clusters (which refer to clusters with the size between subnanometer and several dozen of nanometer) show unique features different from that of bulk due to quantum effects. Therefore, they have attracted much recent attention as new materials because of their possible roles in the fields of electronics, environment, energy, medical care, chemical industry or the like. Generally, smaller metal clusters have higher activity. However, catalysts with smaller size become unstable and are prone to be condensed. Moreover, utilization as materials requires composite formation not to impair the function of nano-size clusters. On the other hand, catalysts recoverable, reusable or usable continuously for a long time with high catalytic activity, are requested even from the standpoint of reduction in environmental loading, effective utilization of resources and energy, which has been recently required to chemical industry. Further, development of transition metal catalysts immobilized in insoluble carriers such as inorganic materials or crosslinked polymers has been actively reviewed, to prevent from mixing metals in products or waste materials, to prepare flow system using column for continuous synthesis or to aim combinatorial synthesis.

However, conventional immobilized transition metal catalysts accompany reduction in activity due to a support with strong binding interaction and have difficulty in prevention of metal release due to a support with weak binding interaction such as adsorption or ionic binding. Additionally, the technique to immobilize transition metal complexes to inorganic carriers or organic polymers through ligands with nitrogen and phosphorous atoms, accompany a number of problems: complicated and expensive synthesis of ligand-containing carriers; difficulty in massive scale preparation; reduction in reaction rate; poisoning by ligands; and large constraints in varieties of reaction. Conventional production methods of metal fine particles are classified into solid phase, liquid phase and gas phase methods. The solid method is not expensive and possible in massive scale preparation except that atomization to nano-particles is difficult. Gas phase method represented by chemical vapor deposition (CVD) is suitable for preparing highly purified and highly crystallized nano-particles except that it is expensive, prone to lead to aggregation, and difficult in massive scale preparation and in production of particles with multi-component system. Therefore, a number of problems remain unsolved. In contrast, liquid phase method is relatively easy in massive scale preparation and has the advantage that design of particle size and particle form is possible depending on the purpose.

Carriers of transition metal nano-size clusters in chemical liquid phase methods are under review for various materials such as alumina, zeolite, silica, hydroxyapatite, carbon nanotube, organic polymers and the like. For example, for immobilization of platinum or rhodium on silica (Non-patent reference 1), an immobilization method of metal clusters, in which a metal with a valency of zero was prepared from a metal salt as a raw material by thermal decomposition or by various reductants, has been frequently used. Frequently used reductants involve metal hydride compounds such as sodium borohydride; silane compounds with hydrogen-silica bonding such as trichlorosilane, trialkylsilane, trialkoxysilane (Non-patent reference 2); compounds with silica-silica bonding such as disilane; and hydrazine. However, inorganic materials immobilized with catalysts are relatively stable for heat or solvents, but difficult in preventing from releasing metals.

Immobilization of transition metal clusters to organic polymers includes generally methods mediated by atoms with liganding property such as nitrogen, oxygen or phosphorus; or functional groups; or by physical encapsulation. According to the reports, there has been a number of palladium (0) clusters supported on organic polymers with bidentatate phosphorous ligand and on organic polymers such as polyamide and polyurea with many unresolved issues such as reduction in reaction rate, aggregation and release of clusters. However, unlike inorganic carriers, polymers swollen in a solvent have the advantage that they are not affected by the limitation of carrier surface area.

On the other hand, unlike the immobolization of single metal species, plural transition metal species supported on the same carrier may hopefully bring about synergistic effects and expression of new functions. For example, Suzuki coupling reaction using copper-palladium mixed nano-clusters has been reported and it is known that a platinum catalyst for fuel battery has higher resistance to poisoning against carbon monoxide by alloying with ruthenium. The technology of immobilizing plural types of metal fine particles to a carrier in arbitral ratio has not been established.

Recently an immobilization method has been developed, wherein the immobilization of transition metal nano-size clusters to organic polymers uses a micro encapsulation method. According to the method, a transition metal is immobilized as clusters with sub-nanometer size by weak coordination with benzene rings of styrenic polymer and shows high catalytic activity. After that, combination of a micro encapsulation method and a technique for crosslinking and micelle formation results in polymer-supported transition metal catalysts keeping high activity and with increased stability (Patent reference 1).

In immobilizing transition metal clusters to an aromatic polymer by the micro encapsulation method, palladium involves (1) a method by ligand exchange using palladium with a valency of 0 such as tetrakis triphenyl phosphine palladium ($Pd(PPh_3)_4$) (Non-patent reference 3) as raw materials, (2) a method with thermal reduction using palladium (II) acetate as a raw material. Additionally, for metals other than palladium, immobilization of platinum, ruthenium, scandium and osmium using tetrakis triphenyl phosphine platinum (Pt $(PPh_3)$ 4), dichlorotris triphenyl phosphine ruthenium ($RuCl_2$ $(PPh_3)_3$), scandium triflate ($Sc(OTf)_3$) and osmium tetraoxide ($O_sO_4$), respectively, as raw materials has been reported.

Polysilane has the metallic features of silicon and delocalized sigma bonds, attracted much attention recently as conductive and optical materials, and is well grounded for mass synthetic method for ceramics materials. Besides, as for the preparation methods of a crosslinked polysilane, there have been known methods based on hydrosilylation between polysilane with silica-hydrogen bonding and crosslinking agents with vinyl groups by a platinum or rhodium catalyst (Patent reference 2); methods of formation of siloxane bond by oxygen oxidation; and methods of formation of thermal or light crosslinking of polysilane with vinyl groups (Non-patent reference 5). As an example of immobilization of transition metal cluster using a polysilane, there has been known a method, wherein polymer-micelle is prepared from block polymer between a polysilane and a poly (methacrylic acid), a shell is formed by crosslinking methacrylic acid of the outer layer, and nano size clusters of gold or palladium are immobilized to polysilane of inner layer (Non-patent reference 6, Patent reference 3). In this example a polysilane is used not as a carrier of clusters, but as a reductant of a metal salt. Furthermore, there have been known methods of so-called non-electrolytic coating. In the methods, metal colloids are precipitated on a polysilane by treating particles with a metal salt aqueous solution, wherein the particles are coated with a polysilane on the surface thereof (Patent reference 4). In this case, a polysilane is used as a reductant.

Non-patent reference 1: J. Mol. Catl. A: Chem. 149, 83-94 (1999).
Non-patent reference 2: Chem. Mater. 1, 106-114 (1989).
Non-patent reference 3: J. Am. Chem. Soc. 127, 2125-2135 (2005).
Non-patent reference 4: Synlett 2005, 813-816.
Non-patent reference 5: J. Organomet. Chem. 300, 327-346 (1986).
Non-patent reference 6: Chem. Lett. 32, 980-981 (2003).
Patent reference 1: Japanese Patent Application Public Disclosure No. 2002-66330
Patent reference 2: Japanese Patent Application Public Disclosure No. H6-49215
Patent reference 3: Japanese Patent Application Public Disclosure No. 2003-147418
Patent reference 4: Japanese Patent Application Public Disclosure No. 2002-4057

Problems to be Solved by the Invention

It is an object of the present invention to provide polymer-supported transition metal catalysts, which have high catalytic activity and are easily prepared on a massive scale and handled, and are recoverable and reusable, as well as methods for their preparation and use.

Means to Solve the Problems

The present inventors has discovered that styrene-polymers are useful for immobilization of transition metal clusters (Patent reference 2 and others), and reviewed and developed a carrier of transition metals and the way of supporting, wherein the transition metal carrier has higher catalytic activity, is effective in immobilizing various transition metals, is prepared on a massive scale, and is easily handled. Resultingly, the present inventors discovered a preparation method suitable for the preparation of polysilane-supported transition metals with high catalytic activity, easy handling, recovery and reuse, wherein the preparation method involves steps of resolving or suspending a polysilane and a transition metal compound in a good solvent of the polysilane; mixing in the presence or absence of reductants; and adding slowly a poor solvent of polysilane leading to phase separation. Moreover, the present inventors discovered that the present method is applicable to various transition metals and applicable easily to massive scale preparation and accomplished the present invention.

In other words, the present invention is a polysilane-supported transition metal catalyst comprising a transition metal and a polysilane compound, wherein the transition metal is supported by the polysilane compound.

Additionally, the present invention is a polysilane/inorganic compound-supported transition metal catalyst comprising a transition metal, a polysilane compound and an inorganic compound, wherein the transition metal is supported by the polysilane compound and the inorganic compound, and the inorganic compound is metal oxide, carbonate, sulfate or phosphate.

DETAILED DESCRIPTION OF THE INVENTION

The polysilane-supported transition metal catalyst of the present invention comprises allowing polysilane compounds to support a transition metal. The polysilane compound is a polymer, whose main chain is linked by Si—Si bonding. The polysilane compound may be any of a homopolymer with single silylene unit, a copolymer with random or regular configuration of different types of silylene units, and a block polymer with linkage of different types of homopolymers. Furthermore, a part of Si—Si bonding of the main chain may be substituted by siloxane bonding (Si—O—Si) or carbosilane structure (Si—CH$_2$—Si). These are inevitably contaminated as impurities or mixed in during reaction with surroundings after production. The content of these bondings is at most about 20% of whole Si—Si bonding.

The weight-average molecular weight of the polysilane compounds is between 2,000 and 500,000, preferably between 5,000 and 300,000. Lower molecular weight may result in difficulty in recovery of the catalyst and in crosslinking, while higher molecular weight may result in reduction in the yield of polymer synthesis and in the solubility to a good solvent during supporting of transition metals.

Also, the main chain of the polysilane compound has preferably an aryl group as a side chain, at least 50% of silylene group that constitutes the main chain of a polysilane compound have preferably aryl groups, and all of the silylene group that constitutes the main chain are preferably bound to aryl group. The silylene group may have either one or two aryl groups. The aryl group may increase the stability of the polymer and the catalyst, and prevent the release of transition metals. Reduction in the percentage of aryl group may sometimes accompany lowered supporting yield of transition metals and oxidative cleavage of Si—Si bonding at the time of mixing a polysilane with a transition metal salt; and release of transition metals during catalytic reaction or post treatment. For example, under the condition, wherein palladium could be supported efficiently on the combination of poly (methylphenylsilane) as a carrier and tetrakis triphenyl phosphine palladium (0) as a transition metal compound, the supporting yield of palladium is reduced for poly (diphenylsilane-co-dimethylsilane) as a carrier (Example 3), and recovery of catalyst after the reaction is lowered for poly (cyclohexyl (methyl) silane) (Example 6). Moreover, mixing a transition metal salt (e.g.; hexachloro platinum (IV) acid) as a transition metal compound with poly (cyclohexyl (methyl) silane) as a carrier results in rapid reduction of the platinum salt, probably due to accompanying oxidation of the polymer at the time of the reduction of the platinum salt.

The aryl group may contain a substituent. At a step of polysilane production, it is possible to introduce various substituents into a phenyl group of polysilane in spite of some restrictions on the substituents depending on the production method (for example, aryl halide group is not suitable for the Kipping method). The carbon numbers of the aryl group are preferably between 6 and 12. The aryl group includes specifically phenyl, naphthyl groups and the like. Their allowable substituents include alkyl, aryl, alkoxy, hydroxyl, halogen atom, silyloxy groups and the like.

The silylene group composing the main chain of the polysilane compounds may further contain alkoxy, silyl, silyloxy, or heterocyclic groups as side chain substituents or hydrocarbon groups possibly with substituents.

The alkoxy group may exemplify lower alkoxy groups, and the silyl groups may exemplify trialkylsilyl groups and others.

The hydrocarbon groups include alkyl, aryl, alkenyl, alkynyl, aralkyl groups and the like with carbon numbers between 1 and 16; preferably alkyl, aryl, and alkenyl groups; and more preferably methyl, benzyl, phenyl, vinyl, cyclohexyl groups and the like.

The heterocyclic group includes pyridyl group.

Both ends of the polysilane main chain may contain the structure of hydrogen atom, hydroxyl, alkoxy, halogen atom, hydrocarbon and the like; or may form a cyclic structure with the other end of the main chain. However, it is generally difficult to confirm the cyclic structure in the case of higher molecular weight of polysilane.

Moreover, it is preferable that more than about 50% of silylene unit composing the main chain of the polysilane compound is diphenylsilylene or methylphenylsilylene, and it is more preferable that the polysilane compound is poly (methylphenylsilane).

These polysilanes are commercially available and also able to be synthesized. Although generally polysilanes are hydrophobic, it is possible to be introduced hydrophilic groups by known chemical conversion.

On the other hand, the transition metals used in the present invention are those from group 3 to group 12 in the periodic table. Most of the transition metals could be supported on the above described polysilane compounds in the form of clusters with a valency of zero, oxides or borides.

The transition metals supported on polysilane compounds are mostly clusters with a valency of zero (e.g. Pd, Pt, Au and the like), while analytical results by ICP of samarium (II) iodide, copper (I) chloride or copper (II) acetate reduced by sodium borohydride highly suggest that samarium or copper may be supported after formation of complex with boron. Also, it is possible that a metal with a valency of zero immediately after reduction may be oxidized later during micro encapsulation, isolation or drying process. Excessive amount of transition metals relative to that of polysilane compounds may lead to lowered supporting yield, enlarged cluster size, and release of metals during use. Additionally, generally decreased amount of transition metals supported on a carrier results in smaller size of clusters.

The amount of transition metal atoms or transition metal compounds supported on a polysilane compound is between 0.01 and 0.5 mmol, and preferably between 0.02 and 0.4 mmol, by converting to the amount of transition metal atom per 1 g of transition metal supported on a polysilane. It is between 0.002 and 0.5 mmol, and preferably between 0.005 and 0.4 mmol, by converting to the amount of transition metal atom per 1 g of polysilane/inorganic compound-supported transition metal.

There is no lower limit for supportable amount, but too low supported amount may result in lowered catalytic activity per unit weight during catalytic reaction. Furthermore, lowered supported amount in forming crosslinking of polysilane compound-supported palladium and platinum to be described in detail later may sometimes result in lowered crosslinking efficiency. It is preferable to support more than 0.02 mmol of transition metal per 1 g of polysilane for forming crosslinking the polysilane compound-supported the above metals by heating, UV light or the like.

A supported transition metal may be kept supported as a metal with a valency of zero, as a transition metal compound of raw materials, or as a variously changed state by oxidation reaction and the like after a single reduction to a valency of zero. These are susceptible to the type of transition metals and method of production. For example, it is expected that most of rare earth metals and transition metals of period 4 are supported as boride or hydride; or transition metals formed complex with halogen atom or oxygen compound. Also, it is expected that gold, platinum, palladium or the like is supported as fine metal clusters with a valency of zero.

There is no special restriction on the method for immobilizing a transition metal to a polysilane compound. One of the preferable examples is shown as follows.

Firstly, a polysilane compound and a transition metal compound, and a reductant if necessary are mixed in a good solvent of the polysilane compound. Here, there are no special restrictions on the order of adding a polysilane compound, a transition metal and a reductant. However, since presence of a polysilane compound in the reaction system during reduction of the transition metal facilitates to stabilize fine transition metal clusters, the polysilane compound is preferably dissolved at the starting time to reduce the transition metal. The good solvent is selected depending on the structure of a polysilane compound and representative polysilane compounds such as poly (methylphenylsilane) and many other polysilane compounds dissolve in tetrahydrofuran, aromatic hydrocarbons, and suitable halogenated hydrocarbons. Here, aromatic hydrocarbons involve benzene, toluene, xylene and the like; and suitable halogenated hydrocarbons involve chloroform, methylchloride, dichloroethane and the like. The mixed solvents thereof are also usable. The volume of a good solvent per a polysilane compound depends on molecular weight and solubility of the polysilane compound, but generally the volume is in the range between 3 and 50 ml per 1 g of a polysilane compound, and preferably between 5 and 20 ml.

There are no special restrictions on the valency of metals and the types of ligands concerning the structure of transition metal compounds mixing with polysilane compounds. The transition metal compounds could be composed of more than or equal to two types of transition metal compounds. The ligands may be anions or neutral ligands. Anions usable could involve halogenide ions such as chloride, bromide, iodide, acetate, triflate, methylate, alkoxide, acetylacetonate, trifluoroacetate, propionate, cyano, hexafluoro acetylacetonate, hydroxide, nitrate, sulfonate, or complex salts and hydrate. Neutral ligands involve various phosphine compounds such as triphenylphosphine and the like, carbonyl, alkene, alkine, π-allyl cyclopentadienyl, benzene, cyclooctadiene, cyclooctatetraene and the like.

More precisely, his (2,4-pentanedionato) titanium (IV) oxide, dichloro titanium diisopropoxide, tetra-n-butyl orthotitanate, tetraethyl orthotitanate, tetraisopropyl orthotitanate, titanium (III) chloride, titanium (IV) chloride, his (2,4-pentanedionato) vanadium (IV) oxide, Vanadium (III) chloride, vanadium (IV) chloride, chromium (III) acetate, chromium (II) chloride, chromium (III) chloride, Chromium (III) nitrate, pyridinium chloro chromate, pyridinium dichromate, tris (2,4-pentanedionato) chromium (III), manganese (II) acetate, manganese (III) acetate, manganese (II) chloride, manganese (II) nitrate, manganese (II) sulfate, his (hexafluoro acetyl acetonate) manganese (II), his (2,4-pentanedionato) manganese (II), tris (2,4-pentanedionato) manganese (III), ferrous (II) acetate, ferric (III) oxalate, ferrous (II) chloride, ferric (III) chloride, ferric (III) nitrate, ferrous (II) sulfate, ferric (III) sulfate, ferrocene (II), n-butylferrocene (II), tris (2,4-pentanedionato) iron (III), cobalt (II) acetate, his (2,4-pentanedionato) cobalt (II), tris (2,4-pentanedionato) cobalt (III), cobalt (II) chloride, cobalt (II) nitrate, nickel (II) acetate, tris (2,4-pentanedionato) nickel (II), nickel (II) chloride, nickel (II) nitrate, nickel (II) oxalate, tetrakis (triphenylphosphine) nickel (O), potassium tetracyanide nickelate (II), cuprous (I) acetate, cupric (II) acetate, cuprous (I) bromide, cupric (II) bromide, cuprous (I) chloride, cupric (II) chloride, cuprous (I) iodide, cupric (II) iodide, cupric (II) nitrate, cupric (II) sulfate, bis(2,4-pentanedionato) cupper (II), potassium cupro (II) tetrachloride, zinc (II) acetate, bis(2,4-pentanedionato) zinc (II), zinc (II) nitrate, zinc (II) sulfate, tetrakis (2,4-pentanedionato) zirconium (IV), zirconocene dichloride (IV), zirconium (IV) chloride, zirconium (IV) ethoxide, zirconium (IV) propoxide, zirconium (IV) nitrate, niobium (V) chloride, niobium (V) ethoxide, molybdenum (II) acetate, molybdenum (III) chloride, molybdenum (IV) chloride, molybdenum (V) chloride, bis(2, 4-pentanedionato) molybdenum (IV) dioxide, ruthenium (III) chloride, rhodium (II) acetate, rhodium (III) chloride, rhodium (III) nitrate, his (1,5-cyclooctadiene)µ,µ'-dichlororhodium, tris (triphenylphosphine) rhodium (I) chloride, palladium (II) acetate, palladium (II) chloride, palladium (II) nitrate, bis(2,4-pentanedionato) palladium (II), tetrakis (triphenylphosphine) palladium (0), tetrachloro palladate (II) potasssium, silver (I) acetate, trifluoro methanesulfonate silver (I), silver (I) chloride, silver (I) nitrate, silver (I) sulfate, p-toluene sulfonate silver (I), cadmium (II) acetate, cadmium (II) chloride, cadmium (II) nitrate, cadmium (II) sulfate, hafnium (IV) acetylacetonate, hafnium (IV) chloride, hafnium (IV) ethoxide, hafnium (IV) isopropoxide, hafnocene dichloride, trifluoro methanesulfonate hafnium (IV), tantalum (V) chloride, tantalum (V) ethoxide, tungsten (IV) chloride, tungsten (IV) ethoxide, tungsten hexacarbonyl, tungstic acid, rhenium (III) chloride, rhenium (IV) chloride, rhenium (V) chloride, rhenium pentacarbonyl chloride, osmium (III) chloride, iridium (III) chloride, iridium (IV) chloride, platinum (II) chloride, platinum (IV) chloride, potassium hexachloro platinumate (IV), hexachloro platinumic acid (IV), tetrakis (triphenylphosphine) platinum (O), potassium tetrachloro platinumate (II), gold chloride (I), gold (III) chloride, gold (III) bromide, potassium tetracyano aurate (III), tetrachloro auric acid (III), gold (I) chloro (triphenylphosphine), mercury (I) acetate, mercury (II) acetate, mercury (I) chloride, mercury (II) chloride, mercury (I) nitrate, mercury (II) nitrate, mercury (I) sulfate, mercury (II) sulfate and the like are usable.

For transition metals of a valency of zero, ligand exchange may allow polysilane compounds to support transition metals (Pd(PPh$_3$)$_4$, Ni(PPh$_3$)$_4$ and others). For example, for the support of tetrakis triphenyl phosphin palladium on poly (methylphenylsilane), the reaction mixture was changed to black color by stirring at room temperature for a time period between a few min and several tens of min in tetrahydrofuran, which is suggestive of the presence of ligand exchange. Moreover, when the ligand exchange is not easily induced by the transition metal compounds with olefin as a ligand, the ligand exchange is easily enhanced by simply heating or by reducing the unsaturated bond using hydrogen gas.

Transition metal salts are usually supported on polysilane compounds by thermal decomposition or reduction treatment, but there are some metal salts, which are supportable without reduction treatment with heating or reductants.

The condition of thermal decomposition is diverse depending on the structure of polysilane compounds, types of good solvents or metal salts. For example, supporting of palladium acetate on poly (methylphenyl silane) in tetrahydrofuran is performed by stirring for a time period between 1 and 2 hr at temperature between 0° C. and room temperature. Since thermal decomposition of palladium acetate takes place normally at 67° C., the reduction reaction in the above reaction is probably promoted by polysilane compounds, but actual roles of polysilane compounds are not clear. For other combination of transition metal salts and polysilane compounds, the conditions are appropriately adjusted as follows: temperature is in the range between room temperature and boiling temperature of the good solvent and reaction period is in the range between several min and several tens hr.

The structure and reaction condition for using reductants should be appropriately selected based on the nature of metal salt, polysilane compound and good solvent.

Reductants are not restricted by their types and involve, for example, metal hydrides, metal-hydrogen complex compounds, borane derivatives, hydrazine derivatives, hydrogen gas and the like as usable redactants. Hydrosilanes are convenient as metal hydrides and exemplify, for example, trichlorosilane; trialkylsilanes such as trimethylsilane and triethylsilane; trialkoxysilanes such as trimethoxysilane and triethoxysilane; dialkoxysilane. Additionally, organic tin hydrides such as triphenyl tin hydride and tri-n-buthyl tin hydride; di-isobuthyl aluminum hydride and the like are also usable. Metal-hydrogen complex compounds exemplify sodium borohydride; lithium aluminum hydride; lithium borohydride; the derivative thereof, wherein a part of hydrogen is subsitituted by alkoxy group or hydrocarbon group; and other metal salts. Borane derivatives exemplify diborane, amine-borane complex, mono- or di-alkylborane. Among them, sodium borohydride, hydrosilane compounds, hydrogen gas and the like are suitable taking into account of cost and security. The temperature for reduction is suitable between the temperature for solidifying the reaction mixture and boiling temperature. Excessively high temperature is prone to result in rapid progress of reduction reaction, and larger and irregular cluster size, while too low temperature needs longer reaction period. Usually, the condition, wherein the reaction finishes in several min to about 30 hr is selected. The reaction mixture, kept abandoned for long time after termination of reduction reaction, may sometimes bring about larger cluster size. Mostly, the reaction mixture becomes colored correspondingly as the reduction proceeds. Use of reductants enables production of a polysilane-supported transition metal from most of transition metal salts.

For using sodium borohydride as a reductant, it is expected that copper, nickel, or samarium is supported on polysilane via formation of boride based on the analytical results of ICP, which will be explained later.

A transition metal is supported on a polysilane compound (micro-encapsulation (MC)) by adding a poor solvent into the reaction mixture with efficient stirring after ligand exchange, thermal decomposition or termination of reduction. Types of poor solvents are different depending on the structure of polysilane compounds. For a number of polysilane compounds such as poly (methylphenylsilane), lower alcohols such as methanol, ethanol, isopropyl alcohol; and aliphatic hydrocarbons such as pentane, hexane, heptane, octane, and the like are suitable. Water, acetone, ether, acetonitrile and the like are sometimes usable depending on the types of good solvents. Moreover, the mixed solvent thereof is sometimes favorable. Particularly, when a reductant generating inorganic salts is used, the use of poor solvents including water enables to remove easily the inorganic salts.

The ratio of the amount of a poor solvent to that of a good solvent is between 0.5 and 20 fold (volume), preferably between 1 and 10 fold. The temperature at the time of addition is preferably between solidification temperature of the reaction mixture and boiling temperature and generally suitable between zero degree and room temperature. The time period for adding a poor solvent is dependent on the volume of the poor solvent added. Since excessively rapid addition is prone to result in inhomogeneous support of a catalyst metal on polysilane, the time period is between several min and 24 hr, and more preferably between 10 min and 6 hr. Dripping a poor solvent results in precipitation of a polysilane compound-supported transition metal. The precipitates are recovered by filtration or by centrifugation after addition of enough volume of a poor solvent. The precipitates recovered are washed with a washing solvent several times without dissolving the polymer, wherein the solvent need not be the same poor solvent used for micro encapsulation. For example, when the polysilane-supported transition metal obtained by using hexane as a poor solvent contains inorganic salts derived from reductants and transition metal salts, the previous described contaminations are removed by washing with water-containing alcohol. When transition metals are supported on polysilane compounds in efficient recovery yield, the filtrate after recovery of precipitates is almost without color. However, the filtrate of inefficient recovery yield is frequently colored. The above method can be easily applied to the support of dissimilar metals. Usually support of dissimilar metals are difficult, since the supporting conditions such as reductants and processing temperature are diversely different depending on the types of transition metal salts and transition metal complexes for preparing transition metal clusters. Since the polysilane compounds used for the present invention are able to support various transition metals under relatively similar conditions, setting of supporting conditions of dissimilar metals is easy. For example, for supporting several types of transition metal halides on poly (methylphenylsilane), the procedure comprising stirring with sodium boron hydride in tetrahydrofuran at room temperature for several hr under refluxing condition, dipping of a poor solvent as hexane or isopropyl alcohol, filtrating the generated precipitates and washing by water-containing alcohol enables efficient support of many types of metals.

The amount of metals supported is determined by absorption spectroscopy, ICP or fluorescent X-ray analysis after drying the obtained polysilane-supported transition metal compound. Highly accurate analytical results can be obtained by removing silicon components by pretreatment and by oxidizing the metals for the analysis. For example, on the analysis of poly (methylphenylsilane)-supported palladium, the polysilane-supported palladium compound is heated in aqua regia and the silicon component is separated from palladium ions by extraction procedures. Then the water phase could be analyzed quantitatively by ICP or atomic absorption spectroscopy.

The polysilane-supported transition metal compound thus obtained becomes insoluble to various solvents due to crosslinking between the main chains of polysilane by heating, photoirradiation, microwave irradiation or chemical reaction using crosslinking reagents. For crosslinking by heating, polysilane-supported transition metal compound is heated in the air or in oxygen environment in solvent-free condition. Crosslinking conditions depend on types of supported metals and the structure of the polysilane. For poly (phenylmethylsilane)-supported platinum or palladium, the heat processing with reaction temperature between 80° C. and 250° C., and preferably between 100° C. and 160° C.; and with reaction period between 1 hr and 24 hr, and preferably between 2 hr and 8 hr leads to a compound insoluble in tetrahydrofuran, toluene, or chloroform. Non-crosslinking polymers and silane oligomers fragmented to low molecular weight are removed by washing with a good solvent after heating. However, transition metals are not released by the treatment with enough heating. The gel percentage ((weight after heating, washing by a good solvent, and drying)/(weight before crosslinking reaction)) by thermal crosslinking is usually between 60 and 100%. For more than 60% of gel percentage, releasing transition metals by washing is negligible. Therefore, the supported amount of a transition metal per unit weight of polymer after crosslinking increases relative to that before crosslinking.

Since the raw material of a polysilane compound without supporting transition metals is never insolubilized under the crosslinking condition of the previous polysilane compound-supported palladium or platinum, it is obvious that supported transition metals play a certain part in the crosslinking reaction. Moreover, it is presumed that the above siloxane is involved in at least a part of crosslinking, since thermal crosslinking is inhibited under anoxic condition, and absorption due to siloxane (Si—O—Si) after crosslinking increases in IR spectrum of a polysilane compound compared to that before crosslinking.

Polysilane compounds could be crosslinked also by photoirradiation. The condition for crosslinking is different depending on the structure of polysilane compounds, types of transition metals and the amount supported. However, generally crosslinking is induced by UV irradiation in powders of polysilane-supported transition metal compound in solvent-free system, or suspension in an aliphatic hydrocarbon such as decane, a poor solvent of polysilane.

Any of continuous spectrum light source such as halogen lamp, various lasers and discontinuous spectrum light source such as mercury lamp is usable. Moreover, the polysilane-supported transition metal compound of the present invention is crosslinkable by micro wave irradiation.

On the other hand, it is possible to induce crosslinking by coupling crosslinkable substituents as side chains to main chains of polysilane compounds and by using known techniques depending on the crosslinkable substituents. Crosslinkable substituents usable include vinyl, alkoxysilyl, epoxy, hydroxide, thiol, carboxyl group and the like.

It is known that a polysilane compound with chlorosilane (Si—Cl) structure is obtainable by treating a polysilane compound containing aromatic ring-silicon bonds with hydrogen chloride gas in the presence of a Lewis acid such as aluminum chloride. The Si—Cl bond is engaged in substitution reaction with various electrophilic agents and is applicable to crosslinking and increased functionalization. For example, treatment with water forms Si—OH bond, which is dehydrated by mild heating to form crosslinking. Also, treatment of a polysilane compound with nucleophilic agents with hydrophilic functional groups such as triethylene glycol monomethyl ether changes the compound to hydrophilic. Polysilane-supported transition metal compounds prepared from hydrophilc polysilane compounds are useful to catalytic reactions in aqueous solvents.

Various derivatization of side chains as well as introduction of crosslinkable substituents to silicon of main chains is possible by known techniques (Japanese Patent Publication 2001-253721). Phenyl groups in side chains can be chloromethylated by chloromethyl ether-tin tetrachloride. Crosslinkable polysilane compounds and hydrophilic polysilane compounds can be produced by the use of the chloromethyl group.

It is interpreted that polysilane-supported transition metal catalysts thus obtained are supported as ultrafine particles stabilized by the interaction of transition metals with aromatic rings or sigma bonds conjugated between Si—Si bond in polysilane compounds; and actually the transition metal catalysts show high catalytic activity to various types of reactions.

Furthermore, transition metal catalysts can be supported on both polysilane compounds and inorganic compounds. Immobilization to an inorganic carrier in addition to polysilane compounds increases the filtrability and stability in most cases. Increased surface area or decreased cluster size frequently enhances the catalytic activity. The usable inorganic carriers include carbonates such as various types of metal oxides, barium carbonates, sulfates such as barium sulfate or phosphates such as hydroxyapatite. Preferably used inorganic compounds (inorganic carriers) include at least a type of metal oxide selected from a group composing alumina, titan, silicon, magnesium or zirconium, wherein the metal oxide is usable as a single metal oxide such as alumina, titania, zirconia or silica; or as complex metal oxides such as zeolite and silica-alumina.

The previously described micro encapsulation method is preferable as a production method of the polysilane/inorganic compound-supported transition metal catalyst. Briefly, the method comprises mixing a transition metal compound with polysilane solution in the presence or absence of a reductant, then adding a poor solvent of polysilane to induce phase separation of polysilane containing transition metals. During the procedures, addition of an inorganic compound before adding a poor solvent leads to production of a polysilane/inorganic compound-supported transition metal catalyst. As for the timing of addition of an inorganic compound, any time before adding a poor solvent is possible, but preferably more than five min before, and more preferably more than 30 min before adding a poor solvent after mixing a transition metal compound with polysilane. The optimal amount of inorganic compound used is different depending on the types of transition metals and the structure of polysilane, but usually between 0.1 and 20 (w/w), and preferably between 1 and 10 (w/w) relative to the amount of polysilane.

It is considered that, similarly to previously described polysilane-supported transition metal catalyst, transition metals in polysilane/inorganic compound-supported transition metal catalyst thus obtained are supported as fine particles stabilized by interactions with an aromatic ring and with sigma bond by conjugation of Si—Si bond in a polysilane compound. However, it is also possible that a part of the transition metals are stabilized by polysilane supported on an inorganic compound. The above catalyst shows high catalytic activity for various types of reactions.

It is expected that the polysilane compound, in the previous polysilane/inorganic compound-supported transition metal catalyst, is supported on an inorganic compound and by physical adsorption. Therefore, similar to the previous polysilane compound-supported transition metal catalyst, good solvents of polysilane compounds and coordinating compounds are apt to induce dissolving polysilane compounds and releasing transition metals. However, heating the polysilane/inorganic compound-supported transition metal catalyst inhibits dissolution of polysilane compounds and release of transition metals by formation of crosslinking between polysilane compounds and by forming bonds between polysilane compounds and inorganic compounds. The similar heating condition to the previous polysilane compound-supported transition metal catalyst can be used, however, anoxic condition (e.g. under reduced pressure or under inert gas such as argon environment) or suspending condition in a poor solvent of a polysilane compound leads to efficient crosslinking formation for polysilane/inorganic compound-supported transition metal calalysts. The poor solvent usable includes solvents with boiling temperature of more than 100° C. and with low solubility for polysilane compounds and preferably includes solvents of chain hydrocarbon with carbon numbers between 8 and 18.

The polysilane-supported transition metal catalyst and polysilane/inorganic compound-supported transition metal catalyst of the present invention can be effectively applied to various types of reduction reactions, oxidation reactions, decomposition reactions, or coupling reactions in liquid phase. For example, a polysilane-supported palladium compound catalyzes hydrogenation reaction, hydrogenated decomposition, Heck reaction, Suzuki-Miyaura coupling reaction, Sonogashira reaction, and carbonylation reaction. Furthermore, the polysilane-supported palladium catalyst shows occasionally high activity without adding ligands in the reaction usually requiring addition of phosphine ligand among the above reactions, and consequently it is useful in its simplicity, economical aspect and environmental compatibility (Example 9). A polysilane-supported palladium compound shows high catalytic activity in hydrosilylation of olefins (Example 14A, 14B, 15) and boronation reaction.

A polysilane-supported copper compound shows high catalytic activity in nitroaldol reactions and is recoverable and reusable (Example 17).

Also, the present polysilane-supported transition metal compounds are useful in gas phase reaction, microreactor, flow system reaction, high pressure reaction, reaction in supercritical fluid and the like, as well as in liquid phase reaction.

These polysilane-supported transition metal catalysts are easily recoverable and reusable in batch method, and are usable continuously for a long time in a flow system reaction. Moreover, since there are almost no release and aggregation of metals from the catalysts, these catalysts have advantages in easy isolation of specified substances, availability of highly purified products, excellent economic efficiency, low environmental loading, effective utilization of resources and energy, high security and others.

Additionally, it is expected that the polysilane-supported transition metal catalysts are applied to catalysts for oxidative decomposition, for dechlorination, desulfurization and others; and to exhaust gas treatment, PCB treatment, quality improvement of light oil, water treatment and others.

EXAMPLES

The following examples illustrate the present invention but it is not intended to limit the scope of the present invention. The molecular weight of polymers was determined by the use of Gel Permission Chromatography (GPC) system (SCL-10A, LC-10AD, RID-10A, CTO-10A, DGU-12A, column: shim-packg PC-803, 804, 8025; Shimazu Corp., Kyoto, Japan), tetrahydrofuran as a solvent and polystyrene as a standard for calibration curve. Infrared absorption spectra (IR) were measured by JASCO FT/IR Type-610 (JASCO Corp., Tokyo, Japan) using KBr tablet method. $^1$H-1-NMR and $^{13}$C-NMR were measured by JEOL JNM-EX-LA400 or JEOL JNM-EX-LA300 (JEOL Ltd., Tokyo, Japan) using deuterated chloroform as a solvent. Metal content in a polymer is determined by fluorescent X-ray analysis (EDX-800; Shimazu) or inductively coupled plasma emission spectroscopy (ICP) (ICPS-7510; Shimazu). Gas chromatography (GC) was measured using GC-17A (Shimazu) and high speed liquid chromatography (HPLC) was measured using (SPD-10A, LC-10AT, C-R6A; Shimazu). Transmission electron microscopy (TEM) was measured using JEOL JEM-1200EXII (JEOL).

Example of Preparation 1A

Preparation of Poly (Methylphenylsilane)

Sodium metal (97 g, 4.2 mol) was added to refluxed tetrahydrofuran (1000 ml), then dichloromethylphenylsilane (2.0 mol) was dropped in over 30 min. The mixture was stirred vigorously for 3 hr under reflux, then cooled to room temperature, and was cooled in an ice bath. Three molar hydrochloric acid (500 ml) was added slowly after addition of toluene (500 ml) to decompose excess sodium. The upper phase (organic phase) was separated from the lower phase; was washed with water, 5% aqueous sodium bicarbonate, water, and saturated sodium chloride solution in order successively; and was dried on anhydrous sodium sulfate. After solubilization of the precipitated sodium chloride by adding water, the lower phase (water phase) was extracted by toluene. The extract was washed with 5% aqueous sodium bicarbonate, water, and saturated aqueous sodium chloride solution in order successively; and was dried on anhydrous sodium sulfate. Each desiccating agent was separated out by filtration and the filtrates were combined and concentrated under reduced pressure. The obtained oily matter was added with methanol and precipitates were recovered by centrifugation. Obtained white solid was dissolved in toluene and the toluene solution was added with isopropyl alcohol to result in reprecipitation. The precipitate was collected by centrifugation; washed with isopropyl alcohol; dried at 55° C. under reduced pressure, and poly (methylphenylsilane) was obtained as white powders. The yield was 135 g (percent yield was 56%). The product was a mixture of polysilane (96%, Mw=32,000, Mn/Mw=2.87) and oligosilane (4%, Mw=1,700, Mn/Mw=1.03).

Example of Preparation 1B

Preparation of Poly (Methylphenylsilane-Co-Diphenylsilane)

Sodium metal (97 g, 4.2 mol) was added to refluxed tetrahydrofuran (1000 ml), then a tetrahydrofuran (200 ml) solution of dichloromethylphenyl silane (1.0 mol) and dichloro diphenylsilane (1.0 mol) was dropped in over 40 min. The mixture was stirred vigorously for 3 hr under reflux, then cooled to room temperature, and was cooled in ice bath. The three molar hydrochloric acid (500 ml) was added slowly after addition of toluene (500 ml) to decompose excess sodium. The upper phase (organic phase) was separated from the lower phase; was washed with water, 5% aqueous sodium bicarbonate, water, and saturated aqueous sodium chloride solution in order successively; and was dried on anhydrous sodium sulfate. After solubilization of the precipitated sodium chloride by adding water, the lower phase (water phase) was extracted by toluene. The extract was washed with 5% aqueous sodium bicarbonate, water, and saturated aqueous sodium chloride solution in order successively; and was dried on anhydrous sodium sulfate. Each desiccating agent was separated out by filtration and the filtrates were combined and concentrated under reduced pressure. The obtained oily matter was added with methanol and precipitates were recovered by centrifugation. Obtained white solid was dissolved in toluene and the toluene solution was added with isopropyl alcohol to result in reprecipitation. The precipitate was collected by centrifugation, washed with isopropyl alcohol; dried at 40° C. under reduced pressure, and poly (methylphenylsilane-co-diphenylsilane) was obtained as white powders. The yield was 149 g.

The product was a mixture of polysilane (70%, Mw=5,400) and oligosilane (25%, Mw=1,900 and 5%, Mw=500).

Example of Preparation 1C

Preparation of Poly (Dimethylsilane-Co-Diphenylsilane)

Sodium metal (71 g, 3.1 mol) was added to refluxed tetrahydrofuran (1800 ml), then a tetrahydrofuran (200 ml) solution of dichlorodiphenylsilane (0.76 mol) and dichlorodimethylsilane (0.76 mol) was dropped in over 1 hr. The mixture was stirred vigorously for 5 hr under reflux, then cooled to room temperature, and was cooled by ice bath. The three molar hydrochloric acid (500 ml) was added slowly after addition of toluene (500 ml) to decompose excess sodium. The upper phase (organic phase) was separated from the lower phase; was washed with water, 5% aqueous sodium bicarbonate, water, and saturated aqueous sodium chloride solution in order successively; and was dried on anhydrous sodium sulfate. After solubilization of the precipitated sodium chloride by adding water, the lower phase (water phase) was extracted by toluene. The extract was washed with 5% aqueous sodium bicarbonate, water, and saturated aqueous sodium chloride solution in order successively; and was dried on anhydrous sodium sulfate. Each desiccating agent was separated out by filtration and the filtrates were combined and concentrated under reduced pressure. The obtained oily matter was added with methanol and precipitates were recovered by centrifugation. Obtained white solid was dissolved in toluene and the toluene solution was added with isopropyl alcohol to result in reprecipitation. The precipitate was collected by centrifugation, washed with isopropyl alcohol, dried at 55° C. under reduced pressure and poly (dimethylsilane-co-diphenylsilane) was obtained as white powders. The yield was 85 g. The product was a mixture of polysilane (66%, Mw=21,000, Mw/Mn=2.13) and oligosilane (34%, Mw=1,900, Mw/Mn=1.04).

Example of Preparation 1D

Preparation of Poly (Cyclohexyl (Methyl) Silane)

Sodium metal (9.7 g, 0.42 mol) was added to refluxed tetrahydrofuran (100 ml), then dichlorocyclohexyl (methyl) silane (0.20 mol) was dropped in over 30 min. The mixture was stirred vigorously for 4 hr under reflux, then cooled to room temperature, and cooled in ice bath. The three molar hydrochloric acid (50 ml) was added slowly after addition of toluene (50 ml) to decompose excess sodium. The upper phase (organic phase) was separated from the lower phase; was washed with water, 5% aqueous sodium bicarbonate, water, and saturated aqueous sodium chloride solution in order successively; and was dried on anhydrous sodium sulfate. After solubilization of the precipitated sodium chloride by adding water, the lower phase (water phase) was extracted by toluene. The extract was washed with 5% aqueous sodium bicarbonate, water, and saturated aqueous sodium chloride solution in order successively; and was dried on anhydrous sodium sulfate. Each desiccating agent was separated out by filtration and the filtrates were combined and concentrated under reduced pressure. The obtained oily matter was added with methanol and precipitates were recovered by centrifugation. Obtained white solid was dissolved in toluene and the toluene solution was added with isopropyl alcohol to result in reprecipitation. The precipitate was collected by centrifugation; washed with isopropyl alcohol; dried at 55° C. under reduced pressure; and poly (cyclohexyl (methyl) silane) was obtained as white powders. The yield was 8.0 g (percent yield was 30%).

The obtained polysilane was analyzed by GPC and the result was:
Mw=21,000, Mn/Mw=1.98.

Quantitative Analytical Method of Transition Metals and Boron

The method for quantifying metals in catalysts supporting transition metals other than platinum was according to the following procedures. A polysilane-supported transition metal (100 mg) was put into a test tube, added with chloroform (2 ml), and treated for 3 min in an ultrasonic cleaning bath. The transition metal was heated gradually to 100° C. to remove chloroform by evaporation; and cooled to room temperature. It was added with sulfuric acid (1 ml), and heated at 150° C. for 2 hr in aluminum block thermostatic chamber. Then, nitric acid (2 ml) was dropped in 2 hr. After the mixture was cooled to room temperature and diluted with water and insoluble materials were filtered out by a membrane filter, the filtrate was diluted to a defined amount (25 ml) and was analyzed quantitatively by ICP. Transition metals in solvent containing polysilane, such as the filtrate produced at the time of support of transition metal on polysilane, were quantified by a similar method to the above, after removing the solvents under reduced pressure. Transition metals in a solution without polysilane, such as in a reaction solution after a catalytic reaction, were measured by fluorescent X-ray analysis as is or after concentration if necessary. The method for quantifying platinum in polysilane-supported platinum catalysts was according to the following procedures.

Polysilane-supported platinum catalysts (100 mg) were put into a test tube, added with water (2 ml) and nitric acid (1 ml), and heated at 200° C. for 2 hr in an aluminum block thermostatic chamber. Then, they were cooled to room temperature, added with nitric acid (1 ml) and hydrofluoric acid (1 ml), and heated again at 200° C. Then, the nitric acid-hydrofluoric acid-treatment was repeated until the solution became transparent. When it became transparent, the contents were dried, cooled to room temperature and added with aqua regia (1 ml) and water (1 ml). The solution was heated again in an aluminum block thermostatic chamber and dried by evaporation. The solid was diluted to a defined amount (25 ml) by the addition of water, and was measured quantitatively by ICP. The calibration curve was prepared by diluting the standard solution of transition metal chloride by diluted sulfuric acid or by diluted hydrochloric acid.

The quantity of boron was measured together with that of the transition metal for a part of polysilane-supported transition metals prepared by the use of boron-containing reductants. As the result, boron was detected in copper and samarium.

Example 1A1

Preparation of Poly (Methylphenylsilane)-Supported Palladium (1)

Poly (methylphenylsilane) (10 g) produced in Example of preparation 1A was dissolved in tetrahydrofuran (80 ml) and was added with tetrakis (triphenylphosphine) palladium (Pd (PPh$_3$)$_4$, 1.0 mmol). The solution was changed from yellow to black during about 10 min stirring at room temperature. After stirring for 16 hr, methanol (320 ml) as a poor solvent was dropped in over 2 hr. The precipitates generated (micro encapsulated palladium) were collected by filtration and washed with methanol on the filter. The obtained gray colored powders were dried at 55° C. under reduced pressure and the polysilane-supported palladium was obtained. The yield: 7.8 g; palladium content: 0.13 mmol (recovery rate: 100%).

The product was easily dissolved in chloroform and tetrahydrofuran, but not in methanol and hexane. According to the result of TEM that clusters with more than 1 nm were not observed, the palladium seems to be supported as clusters with sub-nano size.

Similar reaction by changing the amount of tetrakis (triphenylphosphine) palladium relative to that of polysilane provided palladium-containing poly (methylphenylsilane) with different amount of introduced palladium (Example from 1A2 to 1A4). Also, the yield and Pd content were compared according to the change of good and poor solvents (Example from 1A5 to 1A7). Furthermore, the yield and Pd content were examined according to the change of the reaction period and temperature of micro encapsulation (Example from 1A8 to 1A13). (Table 1)

Example 1B

Preparation of Poly (Methylphenylsilane)-Supported Palladium (2)

Poly (methylphenylsilane) (1.0 g) produced in Example of preparation 1A was dissolved in tetrahydrofuran (8.0 ml) and was added with palladium acetate (Pd(OAc)$_2$, 0.10 mmol) under ice cooled condition. The solution was changed to black color after several min with slight exothermic heat. The solution was added with methanol (40 ml) as a poor solvent in 1 hr after stirring for 8 hr. The precipitates generated (micro encapsulated palladium) were collected by filtration and washed with methanol on the filter. The obtained gray colored powders were dried at 55° C. under reduced pressure and the polysilane-supported palladium was obtained. The yield: 0.85 g; palladium content: 0.11 mmol/g (Pd recovery: 100%). Since clusters with size of more than 1 nm were not observed by TEM, palladium seems to be supported as nano-size clusters.

Example 1C

Preparation of Poly (Methylphenylsilane)-Supported Palladium (3)

By the use of similar procedures to Example 1B, except the addition of sodium borohydride (0.50 mmol) after the addition of palladium acetate (0.1 mmol) and the use of 5% water-containing methanol as a poor solvent, the polysilane-supported palladium was obtained. The yield: 0.79 g; palladium content: 0.12 mmol/g (Pd recovery: 95%).

Example 1D

Preparation of Poly (Methylphenylsilane)-Supported Palladium (4)

By the use of similar procedures to Example 1B, except the addition of triethylsilane (0.50 mmol) after addition of palladium acetate, the polysilane-supported palladium was obtained. The yield: 0.84 g; palladium content: 0.11 mmol/g (Recovery: 92%).

Example 1E

Preparation of Poly (Methylphenylsilane)-Supported Palladium (5)

Poly (methylphenylsilane) (1.0 g) produced in example of preparation 1A was dissolved in tetrahydrofuran (8.0 ml) and was added with palladium nitrate ($Pd(NO_3)_2$, 0.10 mmol) and sodium borohydride (0.50 mmol) on ice. After stirring for 4 hr, 5% water-containing methanol (40 ml) was dropped to the mixture as a poor solvent in 1 hr. The generated precipitates (micro encapsulated palladium) were collected by filtration and washed by methanol on the filter. The obtained powders were dried under reduced pressure and the polysilane-supported palladium was obtained. The yield: 0.88 g; palladium content: 0.095 mmol/g (Pd recovery: 84%).

Example 1F

Preparation of Poly (Methylphenylsilane)-Supported Palladium (6)

By the use of similar procedures to example 1E, except the use of triethyl silane (0.50 mmol) instead of sodium borohydride and methanol as a poor solvent, and the poly silane-supported palladium was obtained. The yield 0.90 g; palladium content: 0.091 mmol/g (Pd recovery: 82%).

Example 1G

Preparation of Poly (Methylphenylsilane)-Supported Palladium (7)

Poly (methylphenylsilane) (1.0 g) produced in example of preparation 1A was dissolved in tetrahydrofuran (8.0 ml) and was added with palladium nitrate ($Pd(NO_3)_2$, 0.10 mmol) on ice. After stirring for 4 hr under a hydrogen atmosphere, methanol (40 ml) was dropped as a poor solvent in 1 hr. The generated precipitates (micro encapsulated palladium) were collected by filtration and washed by methanol on the filter. The obtained powders were dried at 55° C. under reduced pressure and the polysilane-supported palladium was obtained. The yield: 0.89 g; palladium content: 0.11 mmol/g (Pd recovery: 98%).

Example 1H

Preparation of Poly (Methylphenylsilane)-Supported Palladium (8)

By the use of similar reaction and after treatment to example 1E, except the use of palladium chloride ($PdCl_2$, 0.10 mmol) instead of palladium nitrate, the polysilane-supported palladium was obtained. The yield: 0.82 g; palladium content: 0.10 mmol/g (Pd recovery: 82%).

Example 1I

Preparation of Poly (Methylphenylsilane)-Supported Palladium (9)

By the use of similar procedures to example 1H, except that triethylsilane (0.50 mmol) instead of sodium borohydride, and methanol as a poor solvent, the polysilane-supported palladium was obtained. The yield: 0.91 g; palladium content: 0.10 mmol/g (Pd recovery: 91%).

Example 1J

Preparation of Poly (Methylphenylsilane)-Supported Palladium (10)

By the use of similar reaction and after treatment to Example 1G, except the use of palladium chloride ($PdCl_2$, 0.10 mmol) instead of palladium nitrate, the polysilane-supported palladium was obtained. The yield: 0.84 g; palladium content: 0.09 mmol/g (Pd recovery: 76%).

Example 2

Preparation of Poly (Methylphenylsilane-Co-Diphenylsilane)-Supported Palladium Poly (methylphenylsilane-co-diphenylsilane) (2.0 g) synthesized in Example of preparation 1B instead of poly (methylphenylsilane) provided the polysilane-supported palladium by the treatment with tetrakis (triphenylphosphine) palladium ($Pd(PPh_3)_4$, 0.20 mmol) similar to the method of example 1A. The yield: 1.57 g; content: 0.12 mmol/g (Pd recovery: 94%).

Example 3

Preparation of Poly (Dimethylsilane-Co-Diphenylsilane)-Supported Palladium

Poly (dimethylsilane-co-diphenylsilane) (2.0 g) synthesized in Example of preparation 1C instead of poly (methylphenylsilane) provided the polysilane-supported palladium by the treatment with tetrakis (triphenylphosphine) palladium ($Pd(PPh_3)_4$, 0.20 mmol) similar to the method of example 1A. The yield: 0.98 g; palladium content: 0.11 mmol/g (Pd recovery: 54%).

Example 4

Preparation of Poly (Cyclohexyl (Methyl) Silane)-Supporting Palladium

Poly (cyclohexyl(methyl) silane) (1.0 g) synthesized in the Example of preparation 1D instead of poly (methylphenylsilane) provided the polysilane-supported palladium by the treatment with tetrakis (triphenylphosphine) palladium ($Pd(PPh_3)_4$, 0.10 mmol) similar to the method of Example 1A. The filtrate obtained for recovery of the product in Example 1 was without color, while the filtrate of the present Example was colored brown. The yield: 0.78 g; palladium content: 0.10 mmol/g (Pd recovery: 78%).

Example 5

Preparation of Insoluble Poly (Methylphenylsilane)-Supported Palladium

Poly (methylphenylsilane)-supported palladium (0.50 g) synthesized in Example 1A was heated for 6 hr at 140° C. in the air in solvent-free condition, cooled to room temperature, added with tetrahydrofuran (5 ml), stirred for 1 hr at 55° C., filtered, and was washed with tetrahydrofuran, chloroform and methanol. The obtained insoluble matters were dried at 55° C. under reduced pressure, and the insoluble poly (methylphenyl silane)-supported palladium was obtained as black-brown powders. The yield: 0.34 g; palladium content: 0.18 mmol/g (Pd recovery: 94%).

Additionally, poly (methylphenylsilane) (Preparation Example 1A) not containing palladium treated to a similar heating treatment as above dissolves in tetrahydrofuran.

Example 6

Hydrogenation Reaction of Ethyl Cinnamate Using Polysilane-Supported Palladium Catalyst Ethyl cinnamate (1.0 mmol) was dissolved in hexane (2.0 ml), added with polysilane-supported palladium (5 μmol Pd equivalent) obtained in Examples 1 and 4, stirred under a hydrogen atmosphere and measured quantitatively the amount of generated ethyl-3-phenylpropionate after 0.5, and 2 hr by gas chromatography. The results are shown in Table 1 (the second column from the right).

[C1]

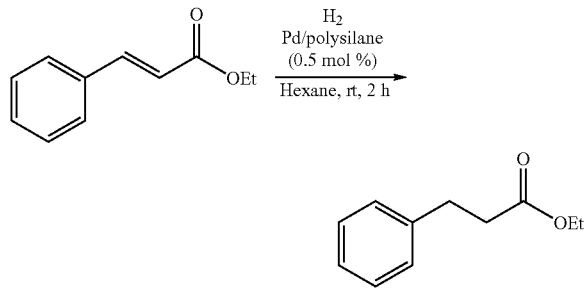

Analytical Condition
Column: J & W Scientific, DB-1 (100% Dimethylpolysiloxane), I. D. 0.25 μm, 60 m
Carrier: He at 20.1 cm/sec, Injector: 200° C., Detector: 250° C.,
Conditions: 100-250° C. at 10° C./min, 250° C. for 10 min
Internal Standard: Naphthalene Furthermore, the examination on recovery and reuse of the catalyst in the present reaction (reaction period was 2 hr) using the catalyst synthesized in Example 1B showed that hydrogenation reaction proceeded quantitatively up to 5 times use, recovery of the catalyst was 97% in average, and released palladium was 0.06% in maximum (0.03% in average). Moreover, most of the catalyst was recovered quantitatively in the hydrogenation reaction of Example 6, while recovery for the catalyst synthesized in Example 4 was 20%. Therefore, it is presumed that side chain phenyl group is effective for the stability of the catalyst.

Example 7

Sonogashira Coupling Reaction Using Polysilane-Supported Palladium Catalyst Iodobenzene (0.40 mmol) and phenylacetylene (0.40 mmol) were dissolved in ethanol (2 ml), and added with potassium carbonate (0.80 mmol) and poly (methylphenylsilane)-supported palladium (0.02 mmol Pd equivalent) obtained in Example 1A1, stirred at 80° C. for 12 hr.

The mixture was separated from catalysts by filtration at room temperature, and washed with ethanol and water. The filtrate was concentrated, added with ethylacetate, washed with water and saturated aqueous sodium chloride. The organic phase was dried by anhydrous sodium sulfate. After the desiccating agents were filtered out, the solvent was evaporated under reduced pressure. The residues were purified by silica gel chromatography and diphenyl acetylene was obtained at the yield of 66%. Palladium was not detected in the filtrate after the reaction (fluorescent x-ray analysis) and the catalyst was recovered quantitatively.

Diphenylacetylene $^1$H-NMR (CDCl$_3$) δ=7.32-7.37 (m, 6H), 7.52-7.55 (m, 4H); $^{13}$C-NMR (CDCl$_3$) δ=89.4, 123.3, 128.3, 128.4, 131.6.

Example 8

Suzuki-Miyaura Coupling Reaction Using Polysilane-Supported Palladium Catalyst 4-Bromo acetophenone (0.40 mmol) and phenyl boric acid (0.40 mmol) were dissolved in ethanol (2 ml), potassium carbonate (0.80 mmol) and poly (methylphenylsilane)-supported palladium (0.02 mmol Pd equivalent) obtained in Example 1A1 and tris (o-tolyl phosphine) (0.02 mmol) were added, stirred at 80° C. for 2 hr. After the catalysts were filtered out at room temperature, the filtrate was washed with ethanol and water. The filtrate was concentrated, added with ethyl acetate, washed with water and saturated aqueous sodium chloride solution, and the organic phase was dried by anhydrous sodium sulfate. After the desiccating agents were filtered out, the solvent was evaporated under reduced pressure. The obtained residues were purified by silica gel chromatography and 4-acetyl biphenyl was obtained at the yield of 94%. Palladium was not detected in the filtrate after the reaction (fluorescent x-ray analysis) and the catalyst was recovered quantitatively. The same reaction was repeated using the recovered catalyst and the product was obtained quantitatively without release of palladium. 4-Acetylbiphenyl: $^1$H-NMR (CDCl$_3$) δ=2.60 (s, 3H), 7.35-7.46 (m, 3H), 7.58-7.66 (m, 4H), 8.00 (d, 2H, J=8.6 Hz); $^{13}$C-NMR (CDCl$_3$) δ=26.5, 127.1, 127.1, 128.1, 128.8, 128.8, 135.7, 139.7, 145.6, 197.6.

Example 9

Suzuki-Miyaura Coupling Reaction Using Polysilane-Supported Palladium Catalyst without Adding External Ligand The reaction of Example 8 was performed without adding tris(o-tolyl phosphine) and 4-acetylbiphenyl was obtained at the yield of 81%. Palladium was not detected in the filtrate after the reaction (fluorescent x-ray analysis) and the catalyst was recovered quantitatively.

Example 10A

Preparation of Poly (Methylphenylsilane)-Supported Platinum

Poly (methylphenylsilane) (10 g) prepared in Preparation Example 1A was dissolved in tetrahydrofuran (80 ml), then added with hexachloro platinic acid 6-hydrate (H2PtCl$_6$.6H$_2$O, 1.0 mmol) at room temperature, added with triethoxysilane (HSi(OEt)$_3$, 10 mmol) at room temperature. The mixture was stirred for 24 hr, dropped hexane (400 ml) as a poor solvent in 1 hr. The precipitates generated were collected by filtration, washed with methanol on the filter. The obtained powders were dried at 55° C. under reduced pressure and the polysilane-supported platinum was obtained. The yield: 8.76 g, platinum content: 0.11 mmol/g (Pt recovery: 96%).

The results obtained under different substrates, reductants and reaction conditions are shown in Table 2.

Example 11

Preparation of Insoluble Polysilane-Supported Platinum

Poly (methylphenylsilane)-supported platinum prepared in Example 10A (5.0 g) was heated at 140° C. for 2 hr in solvent-free system, cooled to room temperature, added with tetrahydrofuran (50 ml), stirred at 55° C. for 1 hr, filtrated, and washed with tetrahydrofuran, chloroform and methanol. The obtained powders were dried at 55° C. under reduced pressure and insoluble poly (methylphenylsilane)-supported platinum was obtained as gray colored powders. The yield: 4.15 g; platinum content: 0.12 mmol/g (Pt recovery: 91%).

Additionally, the yield of the insoluble polysilane-supported platinum crosslinked by heating at 120° C. for 6 hr using the same amount of raw materials was 4.25 g.

Example 12

Hydrogenation Reaction of Diphenyl Acetylene Using Polysilane-Supported Platinum Catalyst Hexane solution (3.0 ml) of diphenyl acetylene (0.25 mmol) was added to polysilane-supported platinum (25 μmol Pt equivalent) obtained in Example 10M, and stirred for 1 hr under a hydrogen atmosphere. After durene was added to the reaction mixture as an inner standard material, the reaction mixture was filtrated, concentrated by evaporation and residues were obtained. Analysis of the residues by $^1$H-NMR showed that 1,2-diphenylethane was produced quantitatively. Also, fluorescent X-ray analysis of the filtrate showed no release of platinum from the catalyst.

1,2-Diphenylethane: $^1$H-NMR (CDCl$_3$) δ=2.96 (s, 4H), 7.16-7.20 (m, 6H), 7.25-7.29 (m, 4H)

Example 13

Hydrogenation reaction of 4-methyl-2,4-diphenylpentene using polysilane-supported platinum catalyst 4-Methyl-2,4-diphenylpentene (1.0 mmol) was hydrogenated by similar method to Example 12. 2-Methyl-2,4-diphenylpentane was produced in 92% yield according to the fluorescent X-ray analysis of the filtrated. Fluorescent X-ray analysis of the filtrate showed no release of platinum from the catalyst.

2-Methyl-2,4-diphenylpentane: $^1$H-NMR (CDCl$_3$) δ=1.02 (d, 3H), 1.14 (s, 3H), 1.24 (s, 3H), 1.49 (dd, 1H, J=5.0, 14.0 Hz), 2.05 (dd, 1H, J=7.2, 14.0 Hz), 2.53 (m, 1H), 7.00-7.29 (m, 10H).
$^{12}$C-NMR (CDCl$_3$) δ=25.1, 28.2, 31.0, 37.0, 38.4, 52.7, 125.4, 125.5, 126.0, 127.0, 127.9, 128.2, 149.2, 149.3.

Example 14A

Hydrosilylation Reaction Using Polysilane-Supported Platinum Catalyst (1)

4,4-Diphenyl-1-butene (compound 1, 0.40 mmol) and pentamethyl disiloxane (0.6 mmol) were dissolved in hexane (2.0 ml), added with poly (methylphenylsilane)-supported platinum (200 mg, 5.5 mol %) prepared in Example 10A and stirred at 20° C. for 2 hr. The filtrate was washed with hexane after separation from catalyst, concentrated, and purified by silica gel column chromatography using hexane as an eluting solvent. (4,4-Diphenylbutyl) pentamethyl disiloxane was obtained as oil without color (140 mg (98%)) and 1,1-diphenyl butane was obtained (2 mg (yield 2%)).

(4,4-Diphenylbutyl) pentamethyl disiloxane: $^1$H-NMR (CDCl$_3$) δ=0.11-0.04 (s×2, 15H), 0.47-0.61 (m, 2H), 1.20-1.39 (m, 2H), 2.06 (dt, J=7.7 Hz), 3.90 (t, 1H, J=7.7 Hz), 7.06-7.29 (m, 10 H)

Example 14B

Hydrosilylation Reaction Using Polysilane-Supported Platinum Catalyst (2)

Triethoxisilane (compound 2, 0.6 mmol) instead of pentamethyldisiloxane was used for the same reaction to Example 14A. $^1$H-NMR analysis with durene as an internal standard material without isolation of products showed that (4,4-diphenylbuthyl) triethoxysilane (compound 3) was produced with the yield of 85%, and 1,1-diphenylbutane (compound 4) was produced with the yield of 6%.

(4,4-Diphenylbutyl) triethoxysilane: $^1$H-NMR (CDCl$_3$) δ=0.62-0.73 (m, 2H), 0.91 (t, 9H, J=7.0 Hz), 1.33-1.49 (m, 2H), 2.00 (dt, 2H, J=7.8 Hz), 3.74 (q, 6H, J=7.0 Hz), 3.91 (t, 1H, J=7.0 Hz), 7.06-7.32 (m, 10H)

The results of similar reaction (the following formula) using polysilane-suppoted platinum prepared with different methods are shown in Table 2 (the second column from the right side). For the catalysts, wherein the introduced amount of platinum is not measured, catalysts were used under the assumption that platinum was recovered quantitatively.

(C2)

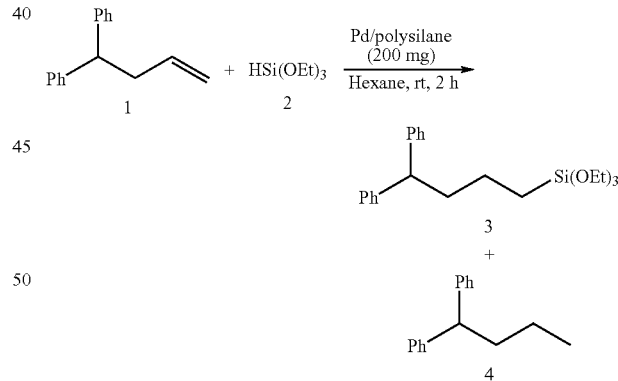

Example 15

Hydrosilylation Reaction Using Insoluble Polysilane-Supported Platinum Catalyst

Similar reaction to Example 14B, except that insoluble poly (methylphenyl silane)-supported platinum (67 mg, 2 mol %) produced in Example 11 was used as a catalyst and stirring was at 20° C. for 29 hr, was performed. (4,4-Diphenylbuthyl) triethoxysilane was produced at 82% and 1,1-diphenylbutane was produced at 1%.

Example 16a

Preparation of Poly (Methylphenylsilane)-Supported Copper (1)

Poly (methylphenylsilane) (2.0 g) prepared in Preparation Example 1A was dissolved in tetrahydrofuran (16 ml), and added with cuprous chloride (CuCl, 0.2 mmol) and sodium borohydride (NaBH$_4$, 0.5 mmol). The mixture was stirred for 12 hr, added with isopropyl alcohol (40 ml) in 30 min, and then with 10% water-containing isopropyl alcohol (40 ml) in 30 min. The generated precipitates were collected by filtration and washed with methanol, water and methanol in order successively on the filter. Poly (methylphenylsilane)-supported copper was obtained after drying the obtained powders with gray green color at 55° C. under reduced pressure. The yield: 1.95 g; copper content: 0.10 mmol/g (Cu recovery: 98%), boron content: 0.046 mmol/g.

Example 16B

Preparation of Poly (Methylphenylsilane)-Supported Copper (2)

Similar procedures to Example 16A, except that copper acetate hydrate (Cu(OAc)$_2$.H$_2$O, 0.2 mmol) was used instead of cuprous chloride, provided poly (methylphenylsilane)-supported cupper.

The yield: 1.97 g; copper content: 0.098 mmol/g (Cu recovery: 97%), Boron content 1.0 mmol/g.

Example 16C

Preparation of Poly (Methylphenylsilane)-Supported Copper (3)

Triethylsilane (Et$_3$SiH, 1.0 mmol) instead of sodium borohydride was used to obtain poly (methylphenylsilane)-supported copper by the procedures similar to Example 16B. The yield: 1.87 g; copper content: 0.059 mmol/g (Cu recovery: 54%)

Example 17

Nitro-Aldol Reaction Using Polysilane-Supported Copper Catalyst

Poly (methylphenylsilane)-supported copper (204 mg, 5 mmol) was added to an ethanol (2.0 ml) solution of p-nitrobenzaldehyde (0.4 mmol) and nitromethane (1.2 mmol), and was stirred at room temperature for 3 hr. The reaction mixture was filtrated, and the filtrate was concentrated, and analyzed by $^1$H-NMR. Resultantly, 2-nitro-1-(4-nitrophenyl) ethanol was produced at the conversion rate of 95%.

2-Nitro-1-(4-nitrophenyl)ethanol: $^1$H-NMR (CDCl$_3$) δ=3.10 (s, 1H), 4.55-4.65 (m, 2H), 5.62 (dt, 1H, J=8.0 Hz), 7.63-7.65 (m, 2H), 8.27-8.31 (m, 2H).

Example 18A

Preparation of Poly (Methylphenylsilane)-Supported Nickel (1)

Poly (methylphenylsilane) (1.0 g) prepared in Preparation Example 1A was dissolved in tetrahydrofuran (8 ml), added with tetrakis (triphenylphosphine) nickel (Ni(PPh$_3$)$_4$, 0.1 mmol), stirred at room temperature for 24 hr and dropped with methanol (40 ml) as a poor solvent in 1 hr. The generated precipitates were collected by filtration, and washed with methanol on the filter. Polysilane-supported nickel was obtained as gray powders after drying at 55° C. under reduced pressure. The yield: 0.94 g; nickel content: 0.073 mmol/g (recovery: 68%).

Example 18B

Preparation of Poly (Methylphenylsilane)-Supported Nickel (2)

Nickelchloride (NiCl$_2$, 0.20 mmol) was used instead of cuprous chloride to provide poly (methylphenylsilane)-supported nickel as white powders according to the procedures similar to Example 16A. The yield: 1.78 g.

Example 19

Preparation of Poly (Methylphenylsilane)-Supprted Cobalt

Cobalt chloride (CoCl$_2$, 0.20 mmol) was used instead of cuprous chloride to provide poly (methylphenylsilane)-supported cobalt as gray powders according to the procedures similar to Example 16A. The yield: 1.65 g.

Example 20A

Preparation of Poly (Methylphenylsilane)-Supported Titanium (1)

Poly (methylphenylsilane) (2.0 g) prepared in Preparation Example 1A was dissolved in tetrahydrofuran (16 ml), added with titanium isopropoxide (Ti (OiPr)$_4$, 0.20 mmol) at room temperature, added with sodium borohydride (NaBH$_4$, 1.0 mmol) in ice bath, and stirred for 12 hr. 5% water-containing methanol (80 ml) was dropped in 1 hr and generated precipitates were collected by filtration. The precipitates were washed with methanol, water and methanol in order successively on a filter. Polysilane-supported titanium was obtained as yellow powders after drying at 55° C. under reduced pressure. The yield: 2.00 g; titanium content 0.080 mmol/g (Ti recovery: 80%); Boron content: 0.078 mmol/g.

Example 20B

Preparation of Poly (Methylphenylsilane)-Supported Titanium (2)

Triethyl silane (Et$_3$SiH, 2.0 mmol) was used instead of sodium boron hydride (NaBH$_4$, 1.0 mmol) to provide poly (methylphenylsilane)-supprted titanium as yellow powders according to the procedures similar to Example 20A. The yield: 2.01 g; titanium content 0.099 mmol/g (Ti recovery: 99%)

Example 21

Preparation of Poly(Methylphenylsilane)-Supported Iron (1)

Ferricchloride 6-hydrate (FeCl$_3$.6H$_2$O, 0.20 mmol) was used instead of cuprous chloride to provide poly (methylphenylsilane)-supported iron as light brown powders according to the procedures similar to Example 16A. The yield: 1.78 g.

Example 22

Preparation of Poly (Methylphenylsilane)-Supported Zinc

Zinc chloride ($ZnCl_2$, 0.20 mmol) was used instead of cuprous chloride to provide poly (methylphenylsilane)-supported zinc as white powders according to the procedures similar to Example 16A. The yield: 1.81 g.

Example 23

Preparation of Poly (Methylphenylsilane)-Supported Zirconium

Poly (methylphenylsilane) (5.0 g) prepared in Preparation Example 1A was dissolved in tetrahydrofuran (80 ml), added with sodium borohydride ($NaBH_4$, 2.0 mmol) and n-propyl alcohol solution (0.44 ml) of zirconium tetraisopropoxide ($Zr(OiPr)_4$, 0.50 mmol), stirred for 24 hr, dropped with methanol (200 ml) in 2 hr, and dropped with 10% water-containing methanol (200 ml) in 2 hr. The generated precipitates were collected by filtration and washed with methanol, water and methanol in order successively on the filter. The obtained white powders were dried at 55° C. under reduced pressure to provide poly (methylphenylsilane)-supported zirconium. The yield: 5.05 g, zirconium content: 0.045 mmol/g (Zr recovery: 46%), Boron content: 0.036 mmol/g.

Example 24A

Preparation of Poly (Methylphenylsilane)-Supported Ruthenium (1)

Poly (methylphenylsilane) (1.0 g) prepared in Preparation Example 1A was dissolved in tetrahydrofuran (8 ml), and added with dichlorotris (triphenylphosphine) ruthenium ($RuCl_2 (PPh_3)_3$, 0.1 mmol). The mixture was stirred at room temperature for 24 hr, added with methanol (40 ml) as a poor solvent in 1 hr. The generated precipitates were collected by filtration and washed with methanol on the filter. Polysilane-supported ruthenium was obtained as gray powders after drying the precipitates at 55° C. under reduced pressure. The yield: 0.90 g.

Example 24B

Preparation of Poly (Methylphenylsilane)-Supported Ruthenium (2)

Poly (methylphenylsilane) (1.0 g) prepared in Preparation Example 1A was dissolved in tetrahydrofuran (8 ml), and added with ruthenium chloride•hydrate ($RuCl_3.nH_2O$, 0.1 mmol) and triethoxysilane (1.0 mmol). The mixture was stirred at room temperature for 24 hr, added with hexane (40 ml) as a poor solvent in 1 hr. The generated precipitates were collected by filtration and washed with methanol on the filter. Polysilane-supported ruthenium was obtained as gray powders after drying the powders at 55° C. under reduced pressure. The yield: 0.70 g.

Example 25A

Preparation of Poly (Methylphenylsilane)-Supported Rhodium (1)

Poly (methylphenylsilane) (1.0 g) prepared in Preparation Example 1A was dissolved in tetrahydrofuran (8 ml), and added with rhodium chloride•3-hydrate ($RhCl_3.3H_2O$, 0.1 mmol) and triethoxysilane (1.0 mmol). The mixture was stirred at room temperature for 24 hr, added with hexane (40 ml) as a poor solvent in 1 hr. The generated precipitates were collected by filtration and washed with methanol on the filter. Polysilane-supported rhodium was obtained as gray powders after drying the powders at 55° C. under reduced pressure. The yield: 0.75 g; rhodium content: 0.058 mmol/g (Rh recovery: 43%).

Example 25B

Preparation of Poly (Methylphenylsilane)-Supported Rhodium (2)

Poly (methylphenylsilane) (1.0 g) prepared in Preparation Example 1A was dissolved in tetrahydrofuran (8 ml), and added with chloro (1,5-cyclooctadiene) rhodium (I) dimer ($[RhCl (COD)]_2$, 0.05 mmol). The mixture was stirred at room temperature for 1 hr under a hydrogen atmosphere, added with methanol (40 ml) as a poor solvent in 1 hr. The generated precipitates were collected by filtration and washed with methanol on the filter. Polysilane-supported rhodium was obtained as gray powders after drying the powders at 55° C. under reduced pressure. The yield: 0.95 g; rhodium content: 0.058 mmol/g (Rh recovery: 55%).

Example 26

Preparation of Poly (Methylphenylsilane)-Supported Osmium

Poly (methylphenylsilane) (1.0 g) prepared in Preparation Example 1A was dissolved in tetrahydrofuran (8 ml), and added with osmium chloride ($osCl_3$, 0.1 mmol) and sodium borohydride (1.0 mmol). The mixture was stirred at room temperature for 24 hr, added with methanol (40 ml) as a poor solvent in 1 hr. The generated precipitates were collected by filtration and washed with methanol on the filter. Polysilane-supported osmium was obtained as black powders after drying the powders at room temperature at ambient pressure. The yield: 0.91 g.

Example 27

Preparation of Poly (Methylphenylsilane)-Supported Iridium

Iridium chloride ($IrCl_4$, 0.20 mmol) was used instead of cuprous chloride to provide polysilane-supported iridium as gray powders according to the similar procedures as Example 16A. The yield: 1.76 g.

Example 28A

Preparation of Poly (Methylphenylsilane)-Supported Gold (1)

Poly (methylphenylsilane) (1.0 g) prepared in Preparation Example 1A was dissolved in tetrahydrofuran (8 ml), and added with chloro aurate 4-hydrate ($HAuCl_4.4H_2O$, 0.1 mmol) and tryethyl silane (1.0 mmol). The mixture was stirred at room temperature for 1 hr, added with methanol (40 ml) as a poor solvent in 1 hr. The generated precipitates were collected by filtration and washed with methanol on the filter. Polysilane-supported gold was obtained as pale pink powders after drying the powders at 55° C. under reduced pressure. The yield: 0.87 g; gold content: 0.107 mmol/g (Au recovery: 93%).

Example 28B

Preparation of Poly (Methylphenylsilane)-Supported Gold (2)

Poly (methylphenylsilane) (1.0 g) prepared in Preparation Example 1A was dissolved in tetrahydrofuran (8 ml), and added with chloro (triphenylphosphine) gold (AuClPPh$_3$, 0.1 mmol) and sodium borohydride (1.0 mmol). The mixture was stirred at room temperature for 24 hr, added with methanol (40 ml) as a poor solvent in 1 hr. The generated precipitates were collected by filtration and washed with methanol on the filter. Polysilane-supported gold was obtained as pale pink powders after drying the powders at 55° C. under reduced pressure. The yield: 0.91 g; gold content: 0.065 mmol/g (Au recovery: 57%).

Example 29

Preparation of Poly (Methylphenylsilane)-Supported Samarium

Poly (methylphenylsilane) (1.0 g) prepared in Preparation Example 1A was dissolved in tetrahydrofuran (8 ml), and added with samarium iodide (SmI$_3$, 0.1 mmol) and sodium borohydride (NaBH$_4$, 1.0 mmol). The mixture was stirred at room temperature for 24 hr, added with methanol (40 ml) in 1 hr. The generated precipitates were collected by filtration and washed with methanol, water and methanol in order successively on the filter. Poly (methylphenylsilane)-supported samarium was obtained after drying the obtained powders of gray green color at 55° C. under reduced pressure. The yield: 0.94 g; samarium content: 0.057 mmol/g (Sm recovery: 54%), boron content: 0.038 mmol/g Example 30

Preparation of Poly (Methylphenylsilane)-Supported Ytterbium

Poly (methylphenylsilane) (3.0 g) prepared in Preparation Example 1A was dissolved in tetrahydrofuran (24 ml), and added with ytterbium chloride (YbCl$_3$, 0.30 mmol) and sodium borohydride (NaBH$_4$, 1.0 mmol). The mixture was stirred for 24 hr, added with methanol (60 ml) in 30 min, and with 10% water-containing methanol (60 ml) in 30 min. The generated precipitates were collected by filtration and washed with methanol, water and methanol in order successively on the filter. Poly (methylphenyl silane)-supported ytterbium was obtained after drying the obtained powders of white color at 55° C. under reduced pressure. The yield: 2.97 g; ytterbium content: 0.094 mmol/g (Yb recovery: 93%); boron content: 0.075 mmol/g.

Example 31

Preparation of Poly (Methylphenylsilane)-Supported (Palladium/Copper)

Poly (methylphenylsilane) (4.0 g) prepared in Preparation Example 1A was dissolved in tetrahydrofuran (32 ml), and added with palladium chloride (PdCl$_2$, 0.20 mmol), cuprous chloride (CuCl, 0.20 mmol) and sodium borohydride (NaBH$_4$, 1.0 mmol) at room temperature. The mixture was stirred for 12 hr, added with isopropyl alcohol (80 ml) in 1 hr and with 10% water-containing isopropyl alcohol (80 ml) in 1 hr. The generated precipitates were collected by filtration and washed with methanol, water and methanol in order successively on the filter. Poly (methylphenyl silane)-supported (palladium/copper) was obtained after drying the obtained powders of gray color at 55° C. under reduced pressure. The yield: 3.87 g; palladium content: 0.043 mmol/g (Pd recovery: 83%); copper content: 0.045 mmol/g (Cu recovery: 88%), boron content: 0.023 mmol/g.

Example 32

Preparation and Hydrosilylation Reaction of Poly (Methylphenylsilane)-Supported (Platinum/Rhodium)

Poly (methylphenylsilane) (2.0 g) prepared in Preparation Example 1A was dissolved in tetrahydrofuran (16 ml), and added with hexachloroplatinate•6-hydrate (H$_2$PtCl$_6$.6H$_2$O, 0.1 mmol), rhodium chloride 3-hydrate (RhCl$_3$ 3H$_2$O, 0.10 mmol) and triethoxysilane (2.0 mmol) at room temperature, stirred for 24 hr, dropped with methanol (80 ml) in 1 hr. The generated precipitates were collected by filtration and washed with methanol, water and methanol in order successively on the filter. Poly (methylphenylsilane)-supported (platinum/rhodium) was obtained after drying the obtained powders of gray color at 55° C. under reduced pressure. The yield: 1.31 g; platinum content: 0.12 mmol/g (Pt recovery: 94%), rhodium content: 0.095 mmol (Rh recovery: 74%). The same reaction to Example 14B using the obtained poly (methylphenylsilane)-supported (platinum/rhodium)(200 mg) showed that (4,4-diphenyl butyl) triethoxysilane (compound 3) and 1,1-diphenylbutane (compound 4) were generated 86% and 12%, respectively.

Example 33

Preparation of Poly (Methylphenylsilane)-Supported (Palladium/Ruthenium)

Poly (methylphenylsilane) (4.0 g) prepared in Preparation Example 1A was dissolved in tetrahydrofuran (32 ml), and added with palladium chloride (PdCl$_2$, 0.36 mmol), ruthenium chloride (RuCl$_3$, 0.36 mmol) and sodium borohydride (3.6 mmol) at room temperature. The mixture was stirred for 12 hr, added with 5% water-containing methanol (160 ml) in 1 hr and the generated precipitates were collected by filtration and washed with methanol, water and methanol in order successively on the filter. Poly (methylphenylsilane)-supported (palladium/ruthenium) was obtained after drying the obtained powders of gray color at 55° C. under reduced pressure. The yield: 2.81 g; palladium content: 0.12 mmol/g (Pd recovery: 94%); ruthenium content: 0.095 mmol/g (Ru recovery: 74%), boron content: 0.068 mmol/g.

Example 34

Silica Gel Supporting of Poly (Methylphenylsilane)-Supported Palladium and Hydrogenation Activity Poly (methylphenylsilane) (2 g) prepared in Preparation Example 1A was dissolved in tetrahydrofuran (16 ml), and added with tetrakis (triphenylphosphine) palladium (Pd (PPh$_3$)$_4$, 0.2 mmol) and silica gel (2.0 g). The mixture was stirred at room temperature for 2 hr, added with methanol (80 ml) as a poor solvent in 2 hr. The generated precipitates were collected by filtration and washed with methanol on the filter. Silica gel supporting polysilane-supported palladium was obtained after drying the obtained powders of brown color at 55° C. under reduced pressure. The yield: 3.43 g.

The obtained polysilane-supported palladium (200 mg) supported by silica gel was heated in solvent-free condition at 140° C. for 4 hr, added with tetrahydrofuran (5 ml), heated at 55° C. for 1 hr. The precipitates were collected, washed by methanol and dried at 55° C. under reduced pressure. Then polysilane-supported palladium crosslinked to silica gel was obtained. The yield: 185 mg.

The above obtained polysilane-supported palladium crosslinked to silica gel (9.3 mg, 0.5 mol % to olefins) was added to a hexane solution of ethyl cinnamate (1.0 mmol), stirred at room temperature under a hydrogen atmosphere for 2 hr. The reaction mixture was filtered and the filtrate was analyzed by gas chromatography to show that 3-phenylethyl propionate was generated quantitatively. Fluorescent x-ray analysis could not detect palladium in the filtrate.

Example 35A

Preparation of (Polysilane/Alumina)-Supported Palladium Catalyst

Poly (methylphenylsilane) (1.0 g) prepared in Preparation Example 1A was dissolved in tetrahydrofuran (8 ml), and added with palladium acetate ($Pd(OAc)_2$, 1.0 mmol) in ice bath and stirred for 1 hr. The mixture was added with activated alumina (Wako Pure Chemical Industry, LTD., Osaka, Japan, 300 mesh, 10 g) at room temperature and was stirred at room temperature for 1 hr. The mixture was added with methanol (40 ml) in 2 hr as a poor solvent, and the generated precipitates were collected by filtration and washed with methanol on the filter. Non-crosslinked (polysilane/alumina)-supported palladium was obtained after drying the obtained powders of gray color at 55° C. under reduced pressure. The yield: 10.6 g; palladium content: 0.0084 mmol/g (Recovery: 85%). Although the catalyst is usable to hydrogenation reaction in alcohol solvent, the catalyst was subjected to thermal crosslinking since palladium was prone to be released in the reaction accompanying heating and addition of base. Briefly, non-crosslinked (polysilane/alumina)-supported palladium (1.0 g) was heated at 140° C. for 2 hr in solvent-free condition in the air. After it was cooled to room temperature, it was washed with tetrahydrofuran, chloroform and methanol in order successively, and dried at 55° C. under reduced pressure to provide crosslinked (polysilane/alumina)-supported palladium (The yield=0.96 g, palladium content=8.3 μmol/g, palladium recovery=81%.)

From Example 35B1 to Example 35B33

Hydrogenation Activity of Crosslinked (Polysilane/Inorganic Compound)-Supported Palladium Various types of crosslinked (polysilane/inorganic compound)-supported palladium were prepared, by change of the inorganic compound and reaction conditions in Example 35A. The properties are compared in terms of the yield of products at 30 min after the start of hydrogenation reaction (C3) similar to Example 6 (Table 3). Argon gas instead of air, and decane solvent instead of solvent-free provided also a crosslinked product with high hydrogenation activity and low palladium release rate in good yield. Also, any of the reactions with extension of the reaction period to 2 hr provided quantitative generation of the product.

[C3]

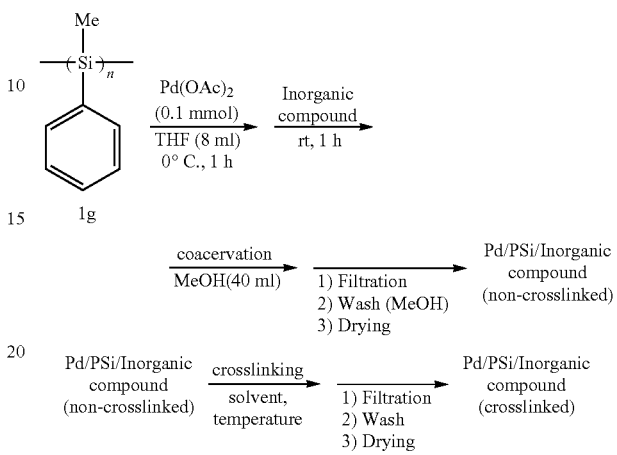

Example 36

Heck Reaction (C4) Using Crosslinked (Polysilane/Inorganic Compound)-Supported Palladium Iodobenzene (1.0 mmol) and ethyl acrylate (2.0 mmol) were dissolved in N-methyl-2-pyrrolidinon (NMP) (2.5 ml), potassium carbonate (1.6 mmol) and [poly(methylphenylsilane)/inorganic compound]-supported palladium (0.002 mmol Pd equivalent) obtained in Example 35A or any of the examples between Example 35B5 and 35B33 were added, stirred at 80° C., and analyzed by gas chromatography. The yield of the product after 2 and 4 hr were determined quantitatively based on the analysis. Catalysts were filtered out from the reaction mixture after 4 hr. Then the filtrate was treated as usual and was analyzed by ICP to quantify palladium. The results are shown in Table 3. Crosslinked [poly (methylphenylsilane)/alumina]-supported palladium used as a catalyst obtained by heating in decane under an argon atmosphere provided high yield of products and the least amount of palladium release in the present reaction (Example 35B17).

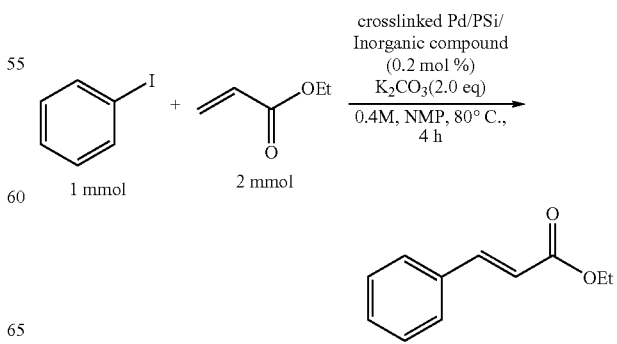

Example 37

Hydrosilylation Reaction in Flow System Using Crosslinked Poly (Methylphenylsilane)-Supported Platinum A glass column (inner diameter: 5 mm; length: 50 mm) was packed with the crosslinked polysilane-supported platinum prepared in Example 10A and was connected to a pump for medium pressure chromatography. Hexane was flowed about 30 min (0.1 ml/min) at room temperature, then hexane solution (0.1 ml/min) of 4,4-diphenyl-1-butene (0.1 mol/l) and triethoxysilane (0.12 mmol/l) was flowed. The effluents collected from the column at every 30 min were concentrated under reduced pressure and analyzed the components by $^1$H-NMR. The results show that (4,4-diphenylbutyl) triethoxysilane, a hydrosilylated compound was generated at the yield more than 70% at the time points from immediately after the start to 4 hr after the start.

TABLE 1

| Example | structure of polysilane and amount used thereof | Pd compound (mmol) | good solvent | reductant (mmol) | reaction time[a] (h) |
|---|---|---|---|---|---|
| 1A1 | (PhSiMe)n (P1) | 10 (g) | Pd(PPh$_3$)$_4$ (1.0) | THF | non | 16 |
| 1A2 | P1 | 1 | Pd(PPh$_3$)$_4$ (0.05) | THF | non | 4 |
| 1A3 | P1 | 1 | Pd(PPh$_3$)$_4$ (0.1) | THF | non | 16 |
| 1A4 | P1 | 1 | Pd(PPh$_3$)$_4$ (0.2) | THF | non | 4 |
| 1A5 | P1 | 1 | Pd(PPh$_3$)$_4$ (0.1) | THF | non | 8 |
| 1A6 | P1 | 1 | Pd(PPh$_3$)$_4$ (0.1) | Toluene | non | 8 |
| 1A7 | P1 | 1 | Pd(PPh$_3$)$_4$ (0.1) | Toluene | non | 8 |
| 1A8 | P1 | 1 | Pd(PPh$_3$)$_4$ (0.1) | THF | non | 1 |
| 1A9 | P1 | 1 | Pd(PPh$_3$)$_4$ (0.1) | THF | non | 2 |
| 1A10 | P1 | 1 | Pd(PPh$_3$)$_4$ (0.1) | THF | non | 4 |
| 1A11 | P1 | 1 | Pd(PPh$_3$)$_4$ (0.1) | THF | non | 8 |
| 1A12 | P1 | 1 | Pd(PPh$_3$)$_4$ (0.1) | THF | non | 4 |
| 1A13 | P1 | 1 | Pd(PPh$_3$)$_4$ (0.1) | THF | non | 4 |
| 1B | P1 | 1 | Pd(OAc)$_2$ (0.1) | THF | non | 8 |
| 1C | P1 | 1 | Pd(OAc)$_2$ (0.1) | THF | NaBH$_4$ (0.5) | 8 |
| 1D | P1 | 1 | Pd(OAc)$_2$ (0.1) | THF | Et$_3$SiH (0.5) | 8 |
| 1E | P1 | 1 | Pd(NO$_3$)$_2$ (0.1) | THF | NaBH$_4$ (0.5) | 4 |
| 1F | P1 | 1 | Pd(NO$_3$)$_2$ (0.1) | THF | Et$_3$SiH (0.5) | 4 |
| 1G | P1 | 1 | Pd(NO$_3$)$_2$ (0.1) | THF | H$_2$ | 4 |
| 1H | P1 | 1 | PdCl$_2$ (0.1) | THF | NaBH$_4$ (0.5) | 4 |
| 1I | P1 | 1 | PdCl$_2$ (0.1) | THF | Et$_3$SiH (0.5) | 4 |
| 1J | P1 | 1 | PdCl$_2$ (0.1) | THF | H$_2$ | 4 |
| 2 | (PhSiMe)$n$-co-(PhSiPh)$m$ | 2 | Pd(PPh$_3$)$_4$ (0.20) | THF | non | 24 |
| 3 | (PhSiPh)$n$-co-(MeSiMe)$m$ | 2 | Pd(PPh$_3$)$_4$ (0.20) | THF | non | 24 |
| 4 | (cHexSiMe)$n$ | 1 | Pd(PPh$_3$)$_4$ (0.10) | THF | non | 24 |

| Example | temp. (° C.) | poor solvent | yield(g) | introduced amount (mmol/g) | yield of hydrogenation(%)[b] | yield of hydrogenation(%)[c] |
|---|---|---|---|---|---|---|
| 1A1 | 25 | MeOH | 7.80 | 0.13 | not performed | |
| 1A2 | 25 | MeOH | 0.81 | 0.06 | 61 | >99 |
| 1A3 | 25 | MeOH | 0.81 | 0.12 | 70 | >99 |
| 1A4 | 25 | MeOH | 0.68 | 0.27 | 80 | >99 |
| 1A5 | 25 | Hexane | 0.65 | 0.13 | 43 | 97 |
| 1A6 | 25 | MeOH | 0.84 | 0.11 | 58 | >99 |
| 1A7 | 25 | Hexane | 0.62 | 0.13 | 44 | 99 |
| 1A8 | 25 | MeOH | 0.69 | 0.14 | 83 | >99 |
| 1A9 | 25 | MeOH | 0.77 | 0.12 | 91 | >99 |
| 1A10 | 25 | MeOH | 0.77 | 0.13 | 83 | >99 |
| 1A11 | 25 | MeOH | 0.79 | 0.12 | 64 | >99 |
| 1A12 | 0 | MeOH | 0.73 | 0.14 | 76 | >99 |
| 1A13 | 40 | MeOH | 0.83 | 0.12 | 64 | >99 |
| 1B | 25 | MeOH | 0.85 | 0.11 | 47 | >99 |
| 1C | 25 | MeOH | 0.79 | 0.12 | 84 | >99 |
| 1D | 25 | MeOH | 0.84 | 0.11 | 65 | >99 |
| 1E | 25 | MeOH | 0.88 | 0.095 | 45 | 90 |
| 1F | 25 | MeOH | 0.90 | 0.091 | 2 | 6 |
| 1G | 25 | MeOH | 0.89 | 0.11 | 3 | 4 |
| 1H | 25 | MeOH | 0.82 | 0.1 | 69 | 95 |
| 1I | 25 | MeOH | 0.91 | 0.1 | 49 | 95 |
| 1J | 25 | MeOH | 0.84 | 0.093 | 59 | 95 |
| 2 | 25 | MeOH | 1.57 | 0.12 | not performed | |
| 3 | 25 | MeOH | 0.98 | 0.11 | not performed | |
| 4 | 25 | MeOH | 0.78 | 0.1 | 75 | >99 |

[a] time period between reaction start and poor solvent addition
[b] yield of ethyl-3-phenylpropionate at 0.5 hr after reaction start (gas chromatography)
[c] yield of ethyl-3-phenylpropionate at 2 hr after reaction start (gas chromatography)

TABLE 2

| Example | poly-(methyl-phenyl silane) (g) | Pt compound (mmol) | good solvent | reductant (mmol) | poor solvent | yield(g) | introduced amount/ recovery (mmol/g)/(%) | yield of hydrosilylation reaction (%) hydro-silylates(3) | reduc-tant (4) |
|---|---|---|---|---|---|---|---|---|---|
| 10A | 10.00 | H$_4$PtCl$_6$•6H$_2$O (1.0) | THF | (EtO)$_3$SiH (10) | MeOH | 8.76 | 0.11/99 | 85 | 6 |
| 10B | 5.00 | H$_4$PtCl$_6$•6H$_2$O (0.50) | THF | Et$_3$SiH (5.0) | MeOH | 4.23 | 0.11/93 | 12 | nd |
| 10C | 2.00 | H$_4$PtCl$_6$•6H$_2$O (0.20) | THF | (EtO)$_3$SiH (2.0) | MeOH | 1.79 | not measured | not performed | |
| 10D | 1.00 | H$_4$PtCl$_6$•6H2O (0.10) | THF | (EtO)$_3$SiH (1.0) | Hexane | 0.75 | not measured | 78 | 13 |
| 10E | 1.00 | H$_4$PtCl$_6$•6H2O (0.10) | Toluene | (EtO)$_3$SiH (1.0) | MeOH | 0.85 | not measured | 79 | 15 |
| 10F | 1.00 | H$_4$PtCl$_6$•6H2O (0.10) | Toluene | (EtO)$_3$SiH (1.0) | Hexane | 0.66 | not measured | 79 | 21 |
| 10G | 2.00 | H$_4$PtCl$_6$•6H$_2$O (0.20) | THF | (MeO)$_3$SiH (2.0) | MeOH | 1.70 | not measured | 71 | 16 |
| 10H | 1.00 | H$_4$PtCl$_6$•6H$_2$O (0.10) | THF | Me$_3$SiOSiMe$_2$H (1.0) | MeOH | 0.86 | not measured | 87 | 13 |
| 10I | 1.00 | H$_4$PtCl$_6$•6H$_2$O (0.10) | THF | NaBH$_4$ (1.0) | MeOH | 0.68 | not measured | not performed | |
| 10J | 1.00 | H$_4$PtCl$_6$•6H$_2$O (0.10) | THF | H$_2$ | MeOH | 0.87 | not measured | not performed | |
| 10K | 1.00 | Pt(COD)$_2$ (0.10) | THF | not used | MeOH | 0.93 | not measured | 80 | 18 |
| 10L | 1.00 | PtCl$_2$(COD) (0.10) | THF | (EtO)$_3$SiH (1.0) | MeOH | 0.77 | not measured | 80 | 6 |
| 10M | 1.00 | PtCl$_2$(COD) (0.26) | THF | NaBH$_4$ (1.3) | MeOH | 0.79 | 0.33/quant. | not performed | |
| 10N | 1.00 | Pt(PPh$_3$)$_4$ (0.086) | THF | not used | MeOH | 0.78 | not measured | not performed | |
| 10O | 1.00 | PtCl$_4$ (0.10) | THF | (EtO)$_3$SiH (1.0) | MeOH | 0.95 | not measured | 74 | 15 |

TABLE 3

| Example | Inorganic compound (g) | non-crosslinlked Pd/PSi/Inorganic compound yield(g)/Pd-supporting amount(mmol/g) | crosslinking condition atomo-sphere | solvent (ml) | temp.(° C.)/time(h) |
|---|---|---|---|---|---|
| 35B1 | SiO$_2$(0.1) | 1.6/0.0458 | air | free | 120/4 |
| 35B2 | | | | | 140/2 |
| 35B3 | | | | | 140/4 |
| 35B4 | Al$_2$O$_3$(0.1) | 0.68/0.126 | air | free | 140/2 |
| 35B5 | | | argon | decane | 140/2 |
| 35B6 | Al$_2$O$_3$(1.0) | 1.6/0.044 | air | free | 100/6 |
| 35B7 | | | | | 120/4 |
| 35B8 | | | | | 120/6 |
| 35B9 | | | | | 140/2 |
| 35B10 | | | | | 140/4 |
| 35B11 | | | | | 160/1 |
| 35B12 | Al$_2$O$_3$(2.0) | 2.5/0.0330 | air | free | 140/2 |
| 35B13 | | | argon | decane | 140/2 |
| 35B14 | Al$_2$O$_3$(5.0) | 5.6/0.0158 | air | free | 140/2 |
| 35B15a | | | argon | free | 140/2 |
| 35B15b[a)] | | | | | |
| 35B15c[b)] | | | | | |
| 35A | Al$_2$O$_3$(10.0) | 10.6/0.0084 | air | free | 140/2 |
| 35B16 | | | air | decane | 140/4 |
| 35B17 | | | argon | decane | 140/4 |
| 35B18 | TiO$_2$(0.1) | 0.80/0.107 | air | free | 140/2 |
| 35B19 | TiO$_2$(1.0) | 1.6/0.048 | air | free | 100/6 |
| 35B20 | | | | | 120/4 |
| 35B21 | | | | | 120/6 |
| 35B22 | | | | | 140/2 |
| 35B23 | | | | | 140/6 |
| 35B24 | TiO$_2$(2.0) | 2.4/0.0372 | air | free | 140/2 |
| 35B25 | TiO$_2$(5.0) | 5.6/0.0141 | air | free | 140/2 |
| 35B26 | TiO$_2$(10.0) | 10.6/0.0066 | air | free | 140/2 |
| 35B27 | ZrO$_2$(1.0) | 1.6/0.043 | air | free | 120/4 |
| 35B28 | | | | | 120/6 |
| 35B29 | | | | | 140/2 |
| 35B30 | | | | | 140/4 |
| 35B31 | ZrO$_2$(2.0) | 2.5/0.0401 | air | free | 140/2 |
| 35B32 | ZrO$_2$(5.0) | 5.6/0.0153 | air | free | 140/2 |
| 35B33 | ZrO$_2$(10.0) | 10.5/0.0080 | air | free | 140/2 |

TABLE 3-continued

| Example | crosslinlked Pd/PSi/Inorganic compound gel rate(g)/ Pd(mmol/g) | Pd recovery (%) | hydrogenation reaction yield (%) | Pd release(%) | Heck reaction yield (%) 2 h | 4 h | Pd release(%) |
|---|---|---|---|---|---|---|---|
| 35B1 | 0.60/0.052 | 57 | not performed | | not performed | | |
| 35B2 | 0.56/0.050 | 51 | 88 | <0.28 | not performed | | |
| 35B3 | 0.68/0.053 | 66 | 63 | np | not performed | | |
| 35B4 | 0.76/0.173 | 90 | 40 | <0.28 | not performed | | |
| 35B5 | 0.38/0.344 | 89 | not performed | | 86 | quant | 7.5 |
| 35B6 | 0.65/0.070 | 74 | 72 | 0.44 | not performed | | |
| 35B7 | 0.84/0.048 | 66 | 89 | 1.7 | not performed | | |
| 35B8 | 0.88/0.052 | 74 | 80 | np | not performed | | |
| 35B9 | 0.77/0.072 | 91 | 55 | np | not performed | | |
| 35B10 | 0.74/0.087 | quant. | 71 | np | not performed | | |
| 35B11 | 0.85/0.086 | quant. | 63 | 0.6 | not performed | | |
| 35B12 | 0.74/0.037 | 69 | 92 | <0.28 | not performed | | |
| 35B13 | 0.90/0.037 | 85 | not performed | | 96 | quant | 4.8 |
| 35B14 | 0.95/0.015 | 81 | 99.8 | <0.28 | 74 | quant | 6 |
| 35B15a | 0.88/0.016 | 79 | not performed | | 77 | quant | 5.5 |
| 35B15b[a] | | | not performed | | 91 | quant | 3 |
| 35B15c[b] | | | not performed | | 79 | quant | 3.8 |
| 35A | 0.96/0.0083 | 85 | 99.8 | <0.28 | 74 | quant | 5.3 |
| 35B16 | 0.96/0.0078 | 79 | not performed | | 87 | quant | 23 |
| 35B17 | 0.96/0.0082 | 83 | not performed | | 97 | quant | 0.5 |
| 35B18 | 0.69/0.156 | 86 | 48 | <0.28 | not performed | | |
| 35B19 | 0.59/0.069 | 67 | 55 | 0.93 | not performed | | |
| 35B20 | 0.79/0.066 | 86 | 83 | <0.29 | not performed | | |
| 35B21 | 0.83/0.047 | 64 | 78 | np | not performed | | |
| 35B22 | 0.79/0.060 | 78 | 74 | np | not performed | | |
| 35B23 | 0.81/0.058 | 77 | 81 | np | not performed | | |
| 35B24 | 0.93/0.035 | 80 | 45 | np | not performed | | |
| 35B25 | 0.99/0.012 | 65 | 76 | <0.28 | 80 | quant | 3.8 |
| 35B26 | 0.97/0.0073 | 74 | >99.9 | <0.28 | 99 | quant | 3.2 |
| 35B27 | 0.80/0.068 | 87 | 87 | <0.29 | not performed | | |
| 35B28 | 0.81/0.064 | 83 | 65 | np | not performed | | |
| 35B29 | 0.80/0.064 | 81 | 46 | np | not performed | | |
| 35B30 | 0.083/0.071 | 94 | 50 | np | not performed | | |
| 35B31 | 0.93/0.039 | 90 | 76 | <0.28 | not performed | | |
| 35B32 | 0.93/0.016 | 90 | 99.3 | <0.28 | not performed | | |
| 35B33 | 0.91/0.0088 | 84 | >99.9 | <0.30 | 67 | quant | 5.4 |

[a] recovery-reuse-once,
[b] recovery-reuse-twice,
np: not performed

What is claimed is:

1. A crosslinked polysilane/inorganic compound-supported transition metal catalyst for liquid phase reaction comprising a transition metal, a polysilane compound and an inorganic compound, wherein the transition metal is supported by the polysilane compound and the inorganic compound to form a polysilane/inorganic compound-supported transition metal catalyst, the polysilane/inorganic compound-supported transition metal catalyst is crosslinked by heating at a temperature between 80 and 160 degree C, the inorganic compound is metal oxide, and the main chain of the polysilane compound contains an aryl group as a side chain.

2. The catalyst of claim 1, wherein the metal of the metal oxide is selected from the group consisting of aluminum, titanium, silicon, magnesium and zirconium.

3. The catalyst of claim 1, wherein the transition metal is a platinum or palladium and the amount of the transition metal atom supported by the polysilane compound and the inorganic compound is more than or equal to 0.02 mmol per 1 g of the polysilane compound.

4. The catalyst of any one of claims 1 to 3, wherein the weight average molecular weight of the polysilane compound is 2,000 to 500,000.

5. A method of performing a reduction reaction, an oxidation reaction, a decomposition reaction or a coupling reaction, the method comprising catalyzing a reduction, oxidation, decomposition, or coupling reaction with a catalyst of claim 1.

6. A crosslinked polysilane/inorganic compound-supported transition metal catalyst for liquid phase reaction comprising a transition metal, a polysilane compound and an inorganic compound, wherein the transition metal is supported by the polysilane compound and the inorganic compound, wherein the polysilane compound comprises a main chain comprising a single type of silylene unit or different types of silylene units, wherein up to 20% of Si—Si bonds in the main chain can be substituted by siloxane bonds (Si—O—Si) or carbosilane bonds (Si—CH$_2$—Si), and wherein at least 50% of the silylene units of the main chain of the polysilane comprise at least one aryl group side chain, and wherein the polysilane/inorganic compound-supported transition metal catalyst is crosslinked by heating to a temperature between 80 and 160 degree C.

7. The crosslinked polysilane/inorganic compound-supported transition metal catalyst of claim 6, wherein the aryl group is selected from phenyl, substituted phenyl, naphthyl, and substituted naphthyl.

* * * * *